US008398964B2

(12) United States Patent  (10) Patent No.: US 8,398,964 B2
Kamei et al.  (45) Date of Patent: Mar. 19, 2013

(54) ORGANOPOLYSILOXANE HAVING AMIDE GROUP, AND COSMETIC MATERIAL CONTAINING SAME

(75) Inventors: Masanao Kamei, Annaka (JP); Toshiki Tanaka, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 296 days.

(21) Appl. No.: 12/844,647

(22) Filed: Jul. 27, 2010

(65) Prior Publication Data

US 2011/0027213 A1    Feb. 3, 2011

(30) Foreign Application Priority Data

Jul. 28, 2009 (JP) ................................. 2009-175065
Jul. 28, 2009 (JP) ................................. 2009-175283

(51) Int. Cl.
*A61K 8/89* (2006.01)
*C08G 77/04* (2006.01)
*A61Q 19/00* (2006.01)

(52) U.S. Cl. .......................... 424/78.03; 528/26; 528/41
(58) Field of Classification Search ............... 424/78.03; 528/41, 26
See application file for complete search history.

(56) References Cited

U.S. PATENT DOCUMENTS

| 6,007,801 A | 12/1999 | Hössel et al. |
| 6,093,240 A * | 7/2000 | Matsumura et al. ..... 106/287.11 |
| 6,576,623 B1 | 6/2003 | Nakanishi et al. |
| 6,592,854 B1 | 7/2003 | Dupuis |
| 2003/0212232 A1 * | 11/2003 | Majeti et al. ..................... 528/10 |
| 2006/0137842 A1 | 6/2006 | Garnier et al. |

FOREIGN PATENT DOCUMENTS

| JP | WO 96/32432 A1 | 10/1996 |
| JP | 9-71504 A | 3/1997 |
| JP | 2002-114849 A | 4/2002 |
| JP | 2007-153751 A | 6/2007 |
| WO | WO 03/095530 A1 | 11/2003 |

OTHER PUBLICATIONS

EP Office Action issued in corresponding EP Application No. 10251338.9 dated Mar. 22, 2012.

EP Search Report dated Sep. 30, 2010, for corresponding EP App. No. 10251338.9.

* cited by examiner

*Primary Examiner* — Anoop Singh
*Assistant Examiner* — Anna Falkowitz
(74) *Attorney, Agent, or Firm* — Birch, Stewart, Kolasch & Birch, LLP

(57) ABSTRACT

Provided are an organopolysiloxane that exhibits good dispersion stability within not only organic oil agents but also cosmetic materials that contain a powder, and is able to produce a cosmetic material that exhibits excellent skin affinity, an organopolysiloxane that does not impart a sticky feeling, and exhibits excellent skin affinity and skin adhesion, and a cosmetic material including such an organopolysiloxane. The organopolysiloxane is represented by formula (1) below:

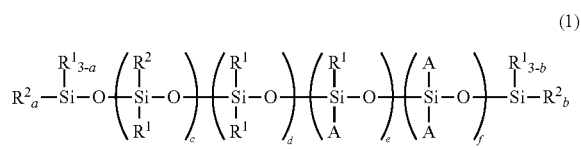

(1)

in which $R^1$ represents a hydrocarbon group such as an alkyl group, $R^2$ represents a group represented by formula (3) or formula (4) below:

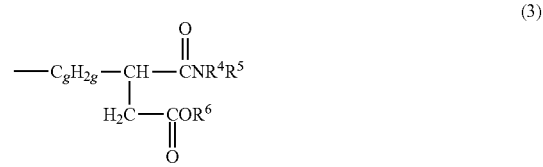

(3)

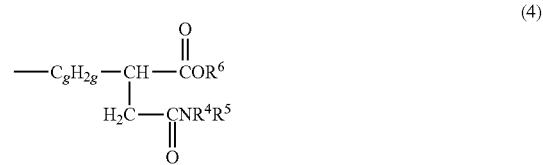

(4)

in which either $R^4$ represents a specific hydrocarbon group and $R^5$ represents a hydrogen atom or a specific hydrocarbon group, or alternatively, at least one of $R^4$ and $R^5$ represents a hydroxyalkyl group, and
A represents a group containing an organosilyl group or organosiloxane residue.

15 Claims, No Drawings

ORGANOPOLYSILOXANE HAVING AMIDE GROUP, AND COSMETIC MATERIAL CONTAINING SAME

BACKGROUND OF THE INVENTION

1. Technical Field of the Invention

The present invention relates to an organopolysiloxane and a cosmetic material containing the organopolysiloxane, and relates specifically to an organopolysiloxane having a specific amide group and a cosmetic material containing that organopolysiloxane.

2. Description of the Prior Art

Because of their relative safety and the like, silicone oils such as dimethylpolysiloxanes are used as oil agents in a wide variety of fields. They are also widely used within cosmetic materials, and in applications such as skin care products and makeup products, low-viscosity silicone oils having a viscosity of 100 $mm^2$/s or less are particularly widely used due to their superior extensibility, feeling of freshness, and level of safety.

However, if the silicone oil is the lone oil agent, then the cosmetic material tends to suffer from unsatisfactory adhesion to the skin and inadequate moisturizing properties. As a result, organic oil agents such as hydrocarbon oils, ester oils and plant-based oils are often used in combination with the silicone oil. However, silicone oils, and particularly dimethylpolysiloxanes, are non-polar oil agents, and when combined with high-polarity ultraviolet absorbers, or high-polarity oil agents such as ester oils and natural animal-based or plant-based oils, tend to be prone to phase separation over time, resulting in long-term stability problems.

In order to address this problem, silicones having phenyl groups or long-chain alkyl groups within the molecule (Patent Document 1) and silicones having long-chain alkyl groups and polyoxyethylene groups within the molecule (Patent Document 2) have been proposed as agents for improving the compatibility of silicone oils and organic oil agents. However, cosmetic materials containing these silicones are unsatisfactory in terms of adhesion to the skin, cosmetic retention, and skin affinity properties.

Compounds in which polar groups such as carboxyl groups or amide groups have been introduced into silicones are also known. For example, silicones having a group represented by the formula shown below (Patent Document 3),

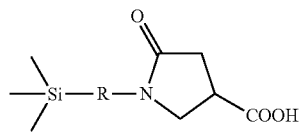

silicones having a group represented by the formula shown below (Patent Document 4),

(wherein M represents a hydrogen atom, alkali metal or ammonium or the like), and silicones having a group represented by the formula shown below (Patent Document 5)

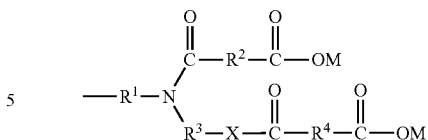

(wherein X represents —O— or —NH—, and M represents a hydrogen atom, metal or ammonium or the like) are already known. The first and second groups listed above contain a single carboxyl group, and the effect of this polar group tends to be inadequate. The third group contains two carboxyl groups, but the fact that preparation of the silicone requires a special amine compound is problematic.

In contrast, acid anhydride-modified silicones can be prepared comparatively easily (Patent Document 6), and amide-modified silicones obtained by reacting such acid anhydride-modified silicones with amines are already known (Patent Document 7). However, these amide-modified silicones are unsatisfactory in terms of factors such as compatibility with the oil agents mentioned above and skin affinity.

Further, because silicone oils such as dimethylpolysiloxanes also have a light feeling, exhibit excellent water repellency and offer superior safety, they are widely used in cosmetic materials. However, silicone oils tend to suffer from sensory type problems, including exhibiting poor affinity with the skin and imparting a slight abrasive feeling to the skin.

In order to improve these types of poor sensory properties that are inherent to silicones, hydrophilic groups are introduced into the silicones. For example, various glycerol-modified silicones are known (for example, see Patent Document 8). Incorporating glycerol-modified residues reduces the slight abrasive feeling of the silicone. However, these glycerol-based oil agents tend to impart a characteristic stickiness, and are also unsatisfactory in terms of the durability of the cosmetic film that is produced.

Silicones in which amide groups have been introduced as hydrophilic groups are also known. For example, Patent Document 3 discloses a silicone having a group represented by the formula shown below,

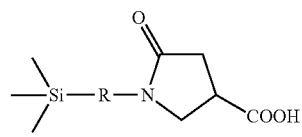

Patent Document 5 mentioned above discloses a silicone having a group represented by the formula shown above, and Patent Document 7 mentioned above discloses a polysiloxane having carboxyl groups in which 50% of those carboxyl groups have undergone amidation using 2-amino-2-methyl-1-propanol, ethanolamine, morpholine or triethanolamine. These compounds are useful as surfactants for aqueous compositions used for cleaning or the like, but are not entirely satisfactory in terms of the feeling produced when applied to the skin.

PRIOR ART DOCUMENTS

[Patent Document 1] JP 2007-153751 A
[Patent Document 2] U.S. Pat. No. 6,576,623
[Patent Document 3] WO 96/32432 A1
[Patent Document 4] U.S. Pat. No. 6,592,854

[Patent Document 5] JP 2002-114849 A
[Patent Document 6] WO 03/095530 A1
[Patent Document 7] U.S. Pat. No. 6,007,801
[Patent Document 8] JP 9-071504 A

SUMMARY OF THE INVENTION

Accordingly, an object of the present invention is to provide an organopolysiloxane which is able to produce a cosmetic material that exhibits favorable compatibility between a silicone oil and a high-polarity ultraviolet absorber or high-polarity organic oil agent such as an ester oil, and also exhibits excellent stability over time, an organopolysiloxane which is able to produce a cosmetic material with excellent skin affinity, an organopolysiloxane that does not impart a sticky feeling and exhibits excellent skin affinity and skin adhesion, and cosmetic materials comprising these types of organopolysiloxanes.

In other words, the present invention provides an organopolysiloxane represented by formula (1) shown below:

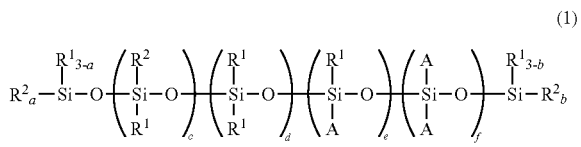
(1)

[wherein each $R^1$ independently represents a group selected from the group consisting of $C_1$ to $C_{30}$ alkyl groups, $C_1$ to $C_{30}$ fluorine-substituted alkyl groups, $C_6$ to $C_{30}$ aryl groups, $C_6$ to $C_{30}$ aralkyl groups, and groups represented by formula (i) shown below:

(i)

(wherein $R^3$ represents a hydrogen atom, $C_1$ to $C_{30}$ aliphatic hydrocarbon group, or organic group represented by $R^7$—(CO)—, $R^7$ represents a hydrogen atom or $C_1$ to $C_{30}$ aliphatic hydrocarbon group, m represents an integer of 0 to 15, i represents an integer of 0 to 50, and j represents an integer of 0 to 50), each $R^2$ independently represents a group selected from the group consisting of groups represented by formula (3) shown below:

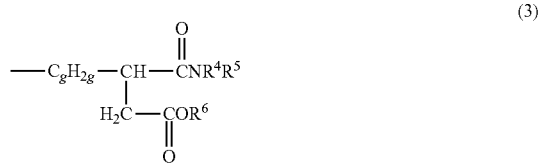
(3)

and groups represented by formula (4) shown below:

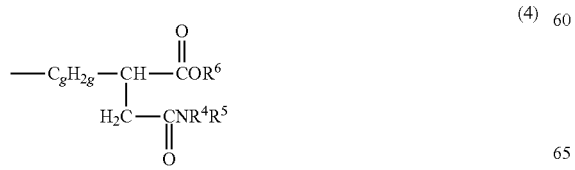
(4)

(in formulas (3) and (4), either
$R^4$ represents a $C_8$ to $C_{40}$ aliphatic hydrocarbon group, $C_8$ to $C_{40}$ aryl group, $C_8$ to $C_{40}$ aralkyl group, or group represented by formula (6) shown below:

(6)

(wherein each of x and y independently represents an integer of 1 to 30, provided that x+y is an integer within a range from 8 to 40, and L represents —NH—, —O—, —COO— or —NHCO—), and $R^5$ represents a hydrogen atom, $C_8$ to $C_{40}$ aliphatic hydrocarbon group, $C_8$ to $C_{40}$ aryl group, $C_8$ to $C_{40}$ aralkyl group, or group represented by formula (6) above, or alternatively
$R^4$ and $R^5$ both represent $C_1$ to $C_{12}$ monohydroxyalkyl groups, or $R^4$ represents a $C_1$ to $C_{12}$ dihydroxyalkyl group and $R^5$ represents a hydrogen atom or $C_1$ to $C_{12}$ alkyl group,
$R^6$ represents a hydrogen atom, alkali metal atom, ammonium ion or alkylammonium ion, and
g represents an integer of 2 to 20),
A is a group represented by formula (5) shown below:

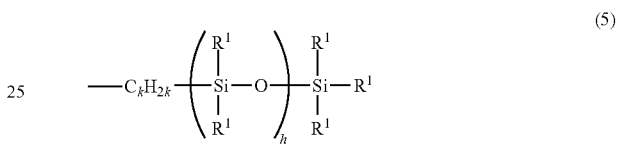
(5)

(wherein $R^1$ is as defined above, k represents an integer of 1 to 5, and h represents an integer of 0 to 500),
a and b each represents an integer of 0 to 3,
c represents an integer of 0 to 100, provided that $1 \leq a+b+c$,
d represents an integer of 0 to 2,000,
e represents an integer of 0 to 500, and
f represents an integer of 0 to 500.

The organopolysiloxane according to the present invention described above contains a specific amide group. In those cases where the organopolysiloxane has a specific hydroxyl-free amide group, it displays excellent compatibility with high-polarity oil agents other than silicones. A cosmetic material containing this type of oil agent and a powder exhibits stable dispersion properties. Accordingly, it is capable of forming a cosmetic material having excellent stability over time and superior skin adhesion properties. Particularly in the case of cosmetic materials comprising a powder, addition of the above organopolysiloxane enables the formation of a cosmetic material in which the powder treatment effects of the organopolysiloxane (namely water resistance, sebum resistance, and dispersion stability within oil agents) result in excellent dispersion of the powder within the cosmetic material. On the other hand, in those cases where the organopolysiloxane described above has a specific amide group containing a hydroxyalkyl group, a cosmetic material can be obtained which has none of the sticky feeling associated with polyglycerol-modified silicones, and exhibits excellent adhesion to the skin and superior cosmetic retention.

DETAILED DESCRIPTION OF THE PREFERRED EMBODIMENTS

In the above formula (1), for $R^1$, examples of the $C_1$ to $C_{30}$ alkyl groups include alkyl groups such as a methyl group, ethyl group, propyl group, butyl group, pentyl group, hexyl group, heptyl group, octyl group, nonyl group and decyl group, and cycloalkyl groups such as a cyclopentyl group and cyclohexyl group. Examples of the $C_1$ to $C_{30}$ fluorine-substituted alkyl groups include a trifluoropropyl group and heptadecafluorodecyl group, examples of the $C_6$ to $C_{30}$ aryl groups include a phenyl group and tolyl group, and examples of the $C_6$ to $C_{30}$ aralkyl groups include a benzyl group and phenethyl group.

$R^1$ may also be a group represented by formula (i) shown below.

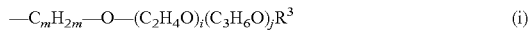

$$—C_mH_{2m}—O—(C_2H_4O)_i(C_3H_6O)_jR^3 \qquad (i)$$

In formula (i), $R^3$ represents a hydrogen atom, $C_1$ to $C_{30}$ aliphatic hydrocarbon group, or organic group represented by $R^7$—(CO)—, wherein $R^7$ represents a hydrogen atom or $C_1$ to $C_{30}$ aliphatic hydrocarbon group, m represents an integer of 0 to 15, and preferably 0 to 5, and i represents an integer of 0 to 50, and preferably 0 to 20. j represents an integer of 0 to 50, and preferably 0 to 20.

Examples of the above $C_1$ to $C_{30}$ aliphatic hydrocarbon groups include alkyl groups such as a methyl group, ethyl group, butyl group, lauryl group, cetyl group or stearyl group, and cycloalkyl groups such as a cyclopentyl group or cyclohexyl group. A methyl group or ethyl group is preferred.

In formula (i), in those cases where m=0, i=0 and j=0, the group is represented by —$OR^3$, and specific examples of the group include $C_1$ to $C_{30}$ alkoxy groups, including lower alkoxy groups such as a butoxy group, and higher alkoxy groups such as an oleyloxy group or stearoxy group. In these cases, the resulting compound may be used in applications that utilize the hydrolyzability of the —$OR^3$ group. If $R^3$ is an organic group represented by $R^7$—(CO)—, then a —O—(CO)—$R^7$ group results, and specific examples of this group include acid residues of acids such as acetic acid, lactic acid, butyric acid, oleic acid, stearic acid and behenic acid.

In formula (i), in those cases where $1 \leq m$, i=0 and j=0, the group is represented by —$C_mH_{2m}$—O—$R^3$, and examples of the group include alkyloxyethyl groups and alkyloxypropyl groups. In this case, m is preferably 3, 5 or 11, and specific examples of the group include a stearyloxypropyl group, behenyloxypentyl group and oleyloxyundecyl group. In those cases where i or j is not 0, a polyoxyalkyleneoxyalkyl group results. In this case, in terms of minimizing oil odor, m is preferably 3 to 11.

$R^1$ is preferably a $C_1$ to $C_{15}$ alkyl group or a phenyl group, and is more preferably a methyl group or butyl group. Moreover, 50% or more of the $R^1$ groups are preferably methyl groups, and compounds in which 70% or more of the $R^1$ groups are methyl groups are the most desirable.

Each $R^2$ independently represents a group selected from the group consisting of groups represented by formula (3) shown below,

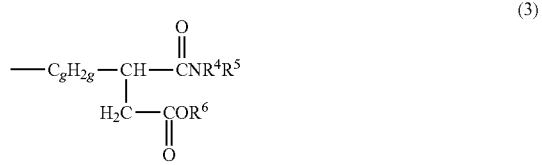

(3)

and groups represented by formula (4) shown below.

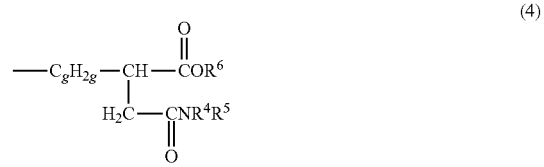

(4)

Embodiment 1

First is a description of an embodiment (hereafter referred to as "embodiment 1") where, in formulas (3) and (4), $R^4$ represents a $C_8$ to $C_{40}$ aliphatic hydrocarbon group (which may be an alicyclic hydrocarbon group), $C_8$ to $C_{40}$ aryl group, $C_8$ to $C_{40}$ aralkyl group, or group represented by formula (6) shown below:

$$—CxH_{2x}-L-C_yH_{2y} \qquad (6)$$

(wherein each of x and y independently represents an integer of 1 to 30, provided that x+y is an integer within a range from 8 to 40, and L represents —NH—, —O—, —COO— or —NHCO—), and $R^5$ represents a hydrogen atom, $C_8$ to $C_{40}$ aliphatic hydrocarbon group, $C_8$ to $C_{40}$ aryl group, $C_8$ to $C_{40}$ aralkyl group, or group represented by formula (6) above.

In those cases where $R^4$ or $R^5$ represents an aliphatic hydrocarbon group, aryl group or aralkyl group, if the number of carbon atoms within the group is less than 8, then the compatibility with polar oil agents other than silicones tends to be unsatisfactory. In contrast, if the number of carbon atoms exceeds 40, then the reactivity of the amino compound used as a raw material with acid anhydrides tends to be poor, resulting in a reduction in the purity of the product organopolysiloxane.

For $R^4$ and $R^5$, specific examples of the $C_8$ to $C_{40}$ aliphatic hydrocarbon group include alkyl groups such as an octyl group, nonyl group, decyl group, lauryl group, cetyl group, stearyl group and behenyl group, alkenyl groups such as an octenyl group, nonenyl group, decenyl group, undecenyl group, dodecenyl group and oleyl group, and cycloalkyl groups such as a propylcyclopentyl group and dimethylcyclohexyl group. Specific examples of the $C_8$ to $C_{40}$ aryl group include an ethylphenyl group, butylphenyl group and naphthyl group, whereas an example of the $C_8$ to $C_{40}$ aralkyl group is a phenethyl group. $R^4$ is preferably a $C_8$ to $C_{30}$ alkyl group, and more preferably a $C_8$ to $C_{20}$ alkyl group, and $R^5$ is preferably a hydrogen atom.

Each of $R^4$ and $R^5$ may also be a group represented by formula (6) shown below.

$$—CxH_{2x}-L-C_yH_{2y} \qquad (6)$$

In formula (6), each of x and y independently represents an integer of 1 to 30, provided that x+y is an integer within a range from 8 to 40, and L represents —NH—, —O—, —COO— or —NHCO—. $R^5$ is preferably a hydrogen atom, $C_8$ to $C_{40}$ aliphatic hydrocarbon group, or a group represented by formula (6), and more preferably a hydrogen atom. In formula (6), x preferably represents an integer of 2 to 25, y preferably represents an integer of 2 to 25, and x+y is preferably an integer of 8 to 30. L is preferably —NH— or —O—.

Embodiment 2

Next is a description of an alternative embodiment (hereafter referred to as "embodiment 2") where, in formulas (3) and (4), either $R^4$ and $R^5$ both represent $C_1$ to $C_{12}$ monohydroxyalkyl groups, or $R^4$ represents a $C_1$ to $C_{12}$ dihydroxyalkyl group and $R^5$ represents a hydrogen atom or $C_1$ to $C_{12}$ alkyl group.

In this embodiment, the organopolysiloxane of the present invention has two hydroxyl groups close to an amide bond, and in this regard is similar to the ceramides that exist in large amounts within the skin. It is thought that this similarity enhances the skin adhesion properties of the compound.

Examples of the $C_1$ to $C_{12}$ monohydroxyalkyl groups include a methylol group, ethylol group, hydroxypropyl group, hydroxybutyl group, hydroxyhexyl group, hydroxycyclohexyl group and hydroxylauryl group. In these groups, the hydroxyl group may be bonded at any position, but is preferably bonded to the group terminal. Further, $R^4$ and $R^5$ may be the same or different.

Examples of the $C_1$ to $C_{12}$ dihydroxyalkyl group include a 1,3-propanediol-2-yl group, 1,2-propanediol-3-yl group, and 1,4-butanediol-2-yl group.

Examples of the $C_1$ to $C_{12}$ alkyl group include a methyl group, ethyl group, hexyl group and lauryl group.

In a preferred configuration, $R^4$ and $R^5$ are both methylol groups, or $R^4$ is a 1,3-propanediol-2-yl group or 1,2-propanediol-3-yl group and $R^5$ is a hydrogen atom.

$R^6$ is a cationic group, and examples include a hydrogen atom, an alkali metal atom such as lithium, sodium or potassium, or an ammonium ion or alkylammonium ion. In a preferred configuration, $R^6$ represents a hydrogen atom or a sodium or potassium atom, and is most preferably a hydrogen atom.

In formulas (3) and (4), g represents an integer of 2 to 20, and preferably 2 to 10.

A is a group represented by formula (5) shown below.

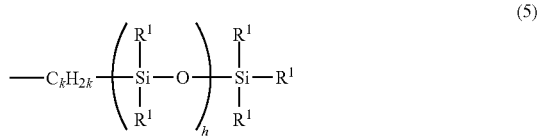

In formula (5), $R^1$ is as defined above, k represents an integer of 1 to 5, and preferably 2 to 4, and h represents an integer of 0 to 500, preferably 3 to 100, and more preferably 3 to 60.

In formula (1), a and b each represents an integer of 0 to 3, and c represents an integer of 0 to 100, and preferably 0 to 50, provided that a+b+c is an integer of 1 or greater, preferably 1 to 50, and more preferably 1 to 30. Organopolysiloxanes in which the value of a+b+c exceeds 100 have a high viscosity and are difficult to handle.

d represents an integer of 0 to 2,000, and preferably 0 to 500. e represents an integer of 0 to 500, and preferably 0 to 100, and f represents an integer of 0 to 500, and preferably 0 to 100.

The polystyrene-equivalent number average molecular weight of the organopolysiloxane, measured by GPC, is preferably within a range from 300 to 300,000, and is more preferably from 500 to 100,000. Particularly when the organopolysiloxane is used as a dispersant for a powder, this number average molecular weight is preferably within a range from 500 to 10,000, and more preferably from 500 to 5,000.

The organopolysiloxane of the present invention is preferably represented by formula (2) shown below.

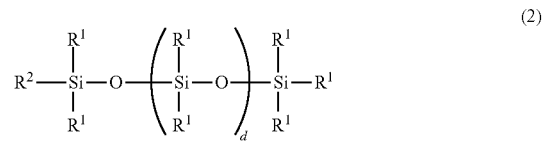

In formula (2), $R^1$ and $R^2$ are as defined above, d represents an integer of 0 to 200, preferably 0 to 100, more preferably 10 to 80, and most preferably 10 to 50.

The organopolysiloxane of the present invention can be synthesized using the method described below.

(Step 1) An organohydrogenpolysiloxane and a compound represented by formula (9) shown below are subjected to an addition reaction in the presence of a platinum catalyst or rhodium catalyst, thereby synthesizing an acid anhydride group-containing organopolysiloxane.

(In formula (9), g is as defined above)

(Step 2) The acid anhydride group-containing organopolysiloxane synthesized in step 1 and a primary or secondary amino compound are reacted, thereby causing a ring opening of the acid anhydride group. The resulting carboxylic acid is then reacted with sodium hydroxide or ammonia water or the like, yielding a product in which $R^6$ is an alkali metal atom or an ammonium ion.

Examples of the compound represented by the above formula (9) include succinic anhydride derivatives such as vinylsuccinic anhydride, allylsuccinic anhydride and hexenylsuccinic anhydride, and of these, allylsuccinic anhydride is preferred.

In those cases where the organopolysiloxane of the present invention includes an $R^1$ group represented by the above formula (i), a compound having an unsaturated group and a polyoxyalkylene group, represented by formula (7) shown below:

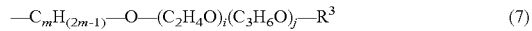

$$-C_mH_{(2m-1)}-O-(C_2H_4O)_i(C_3H_6O)_j-R^3 \quad (7)$$

is supplied to the addition reaction in step 1, together with the compound of formula (9) shown above. Further, in those cases where the organopolysiloxane includes a group represented by the above formula (5), a silicone compound having an unsaturated group represented by formula (8) shown below is supplied to the addition reaction together with the compound of formula (9) shown above.

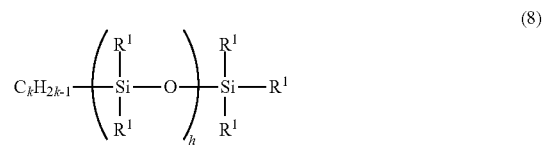

(In formulas (7) and (8), $R^1$, $R^3$, m, i, j, k and h are as defined above)

In step 1, the reaction ratio between the organohydrogenpolysiloxane and the combination of the unsaturated group-containing compounds represented by formulas (7), (8) and (9) is set so that the molar ratio between SiH groups and unsaturated groups is within a range from 0.5 to 2.0, and preferably from 0.8 to 1.2.

Furthermore, the above addition reaction is preferably conducted in the presence of a platinum catalyst or rhodium catalyst, and examples of preferred catalysts include chloroplatinic acid, alcohol-modified chloroplatinic acid, and chloroplatinic acid-vinylsiloxane complexes. The amount used of the catalyst need only be an effective catalytic amount, and the amount of platinum or rhodium is typically not more than 50 ppm, and preferably 20 ppm or less.

If required, the above addition reaction may be performed within an organic solvent, and examples of solvents that may be used include aromatic hydrocarbons such as toluene and xylene, aliphatic hydrocarbons such as n-pentane and n-hexane, alicyclic hydrocarbons such as cyclohexane, halogenated hydrocarbons such as dichloromethane, chloroform and carbon tetrachloride, ethers such as tetrahydrofuran and dioxane, and ketones such as acetone and methyl ethyl ketone. The reaction is preferably conducted either with no solvent, or in a hydrocarbon solvent or ether-based solvent.

There are no particular restrictions on the addition reaction conditions, and in those cases where a solvent is used, reaction is preferably conducted under reflux for a period of 1 to 10 hours.

Examples of the primary or secondary amino compound used in step 2, in the case of embodiment 1, include linear or branched alkylamines such as octylamine, nonylamine, decylamine, laurylamine, cetylamine, stearylamine, oleylamine and behenylamine, cycloalkylamines such as propylcyclopentylamine and dimethylcyclohexylamine, aromatic amines such as ethylaniline, butylaniline, phenethylamine and naphthylamine, diamines such as N-hexylethylenediamine and N-decylethylenediamine, amino ethers such as decyloxyethylamine and lauroxyethylamine, and secondary amino compounds such as N-ethylhexylamine, N-hexyldecylamine and N-hexyllaurylamine.

Examples of the primary or secondary amino compound used in step 2, in the case of embodiment 2, include primary amino alcohol compounds such as 2-aminoethanol, 2-aminopropanol, 3-aminopropanol, 6-aminohexanol, 5-aminohexanol, 2-aminocyclohexanol, 12-aminolauryl alcohol, 2-amino-1,3-propanediol, 3-amino-1,2-propanediol, 2-amino-1,4-butanediol and 2-amino-1,3-butanediol, and secondary amino alcohol compounds such as diethanolamine, dipropanolamine, N-ethylethanolamine, N-hexylethanolamine and N-laurylethanolamine. Of these, 2-amino-1,3-propanediol, 3-amino-1,2-propanediol and diethanolamine are preferred.

The above ring opening reaction proceeds favorably even without a catalyst, although an inorganic salt such as potassium acetate or sodium acetate may be used as a catalyst. Further, if required, the reaction may be performed within a solvent, and examples of organic solvents that may be used include aromatic hydrocarbons such as toluene and xylene, aliphatic hydrocarbons such as n-pentane and n-hexane, alicyclic hydrocarbons such as cyclohexane, halogenated hydrocarbons such as dichloromethane, chloroform and carbon tetrachloride, ethers such as tetrahydrofuran and dioxane, and ketones such as acetone and methyl ethyl ketone. The reaction is preferably conducted either with no solvent, or in a hydrocarbon solvent or ether-based solvent.

The organopolysiloxane of the present invention can be used favorably as a cosmetic material applied externally to the skin or hair.

The organopolysiloxane of embodiment 1 is particularly ideal as an emulsifier within a cosmetic material containing a silicone typically used in cosmetic materials and a polar solvent such as water, a glycol, an ester oil or a glyceride oil, or as a dispersant within a cosmetic material containing a powder.

The organopolysiloxane of embodiment 2 exhibits excellent compatibility with the skin, and is therefore ideal as a component for all manner of products applied externally to the skin, not only cosmetic materials.

The blend amount of the organopolysiloxane of the present invention is typically within a range from 0.1 to 40% by mass, and preferably 0.5 to 20% by mass, of the total mass of the cosmetic material. In the case of a cosmetic material containing a powder, the amount of the organopolysiloxane is typically within a range from 5 to 40 parts by mass, and preferably 5 to 30 parts by mass per 100 parts by mass of the powder.

A cosmetic material of the present invention may include one or more oil agents, depending on the purpose of the cosmetic material. Any oil agent typically used in cosmetic materials may be used, including solid, semi-solid and liquid oil agents. Examples of oil agents that may be used include natural animal-based and plant-based oils and fats, semi-synthetic oils and fats, hydrocarbon oils, higher alcohols, ester oils, commonly used silicone oils, and fluorine-based oil agents.

Specific examples of the natural animal-based and plant-based oils and fats and semi-synthetic oils and fats include avocado oil, linseed oil, almond oil, ibota wax, perilla oil, olive oil, cacao butter, kapok wax, kaya oil, carnauba wax, liver oil, candelilla wax, refined candelilla wax, beef tallow, neat's-foot tallow, beef bone tallow, hardened beef tallow, apricot kernel oil, whale wax, hardened oil, wheat germ oil, sesame oil, rice germ oil, rice bran oil, sugarcane wax, camellia sasanqua oil, safflower oil, shea butter, Chinese tung oil, cinnamon oil, jojoba wax, squalane, squalene, shellac wax, turtle oil, soybean oil, tea berry oil, camellia oil, evening primrose oil, corn oil, lard, rapeseed oil, Japanese tung oil, bran wax, germ oil, horse tallow, persic oil, palm oil, palm kernel oil, castor oil, hardened castor oil, castor oil fatty acid methyl ester, sunflower oil, grapeseed oil, bayberry wax, jojoba oil, macadamia nut oil, beeswax, mink oil, meadowfoam oil, cottonseed oil, cotton wax, Japan wax, Japan wax kernel oil, montan wax, coconut oil, hardened coconut oil, tri(coconut oil fatty acid) glyceride, mutton tallow, peanut oil, lanolin, liquid lanolin, reduced lanolin, lanolin alcohol, hard lanolin, lanolin acetate, lanolin alcohol acetate, lanolin fatty acid isopropyl ester, POE lanolin alcohol ether, POE lanolin alcohol acetate, lanolin fatty acid polyethylene glycol, POE hydrogenated lanolin alcohol ether, and egg-yolk oil. In the above names, POE represents polyoxyethylene.

Examples of the hydrocarbon oils include linear, branched and volatile hydrocarbon oils. Specific examples of these hydrocarbon oils include ozokerite, α-olefin oligomers, light isoparaffin, isododecane, isohexadecane, light liquid isoparaffin, squalane, synthetic squalane, plant-based squalane, squalene, ceresin, paraffin, paraffin wax, polyethylene wax, polyethylene-polypropylene wax, (ethylene-propylene-styrene) copolymers, (butylene-propylene-styrene) copolymers, liquid paraffin, liquid isoparaffin, pristane, polyisobutylene, hydrogenated polyisobutene, microcrystalline wax and Vaseline, and specific examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, POE cholesterol ether, monostearyl glycerol ether (batyl alcohol) and monooleyl glyceryl ether (selachyl alcohol).

Specific examples of the ester oils include diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, isopropyl lauroyl sarcosinate and diisostearyl malate, whereas specific examples of the glyceride oils include acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate and diglyceryl myristate isostearate.

Examples of the silicone oils include low-viscosity to high-viscosity linear or branched organopolysiloxanes such as dimethylpolysiloxane, tris(trimethylsiloxy)methylsilane, caprylyl methicone, phenyl trimethicone, tetrakistrimethylsiloxysilane, methylphenylpolysiloxane, methylhexylpolysiloxane, methylhydrogenpolysiloxane and copolymers of dimethylsiloxane and methylphenylsiloxane, cyclic organopolysiloxanes such as octamethylcyclotetrasiloxane, decamethylcyclopentasiloxane, dodecamethylcyclohexasiloxane, tetramethyltetrahydrogencyclotetrasiloxane and tetramethyltetraphenylcyclotetrasiloxane, amino-modified organopolysiloxanes, pyrrolidone-modified organopolysiloxanes, pyrrolidone carboxylic acid-modified organopolysiloxanes, silicone rubbers such as gum-like dimethylpolysiloxanes having high polymerization degrees, gum-like amino-modified organopolysiloxanes and gum-like copolymers of dimethylsiloxane and methylphenylsiloxane, cyclic organopolysiloxane solutions of silicone gums or silicone rubbers, trimethylsiloxysilicates and cyclic siloxane solutions of trimethylsiloxysilicates, higher alkoxy-modified silicones such as stearoxysilicone, higher fatty acid-modified silicones, alkyl-modified silicones, long chain alkyl-modified silicones, amino acid-modified silicones, fluorinated silicones, silicone resins and silicone resin solutions.

Specific examples of the fluorine-based oil agents include perfluoropolyether, perfluorodecalin and perfluorooctane. The blend amount of the above oil agents varies depending on the cosmetic material formulation, but is typically within a range from 1 to 98% by mass of the entire cosmetic material.

Water may be added to the cosmetic material of the present invention depending on the intended purpose of the material. The blend amount of water varies depending on the material formulation, but is typically within a range from 1 to 95% by mass of the entire cosmetic material.

Depending on the intended purpose, the cosmetic material of the present invention may also include one or more $C_2$ to $C_5$ lower monoalcohols or $C_2$ to $C_{10}$ polyhydric alcohols. Specific examples of these alcohols include lower alcohols such as ethanol and isopropanol, sugar alcohols such as sorbitol and maltose, sterols such as cholesterol, sitosterol, phytosterol and lanosterol, and polyhydric alcohols such as butylene glycol, propylene glycol, dibutylene glycol and pentylene glycol. The blend amount of this alcohol is preferably within a range from 0.1 to 98% by mass of the entire cosmetic material.

Depending on the intended purpose, the cosmetic material of the present invention may also employ a water-soluble or water-swellable polymer. Of such polymer compounds, the use of one or more water-soluble thickeners selected from amongst plant-based polymers, microbial polymers, animal-based polymers, starch-based polymers, cellulose-based polymers, alginic acid-based polymers, polyoxyethylene polyoxypropylene copolymer-based polymers, acrylic polymers and inorganic water-soluble polymers is preferred. Specific examples include plant-based polymers such as gum arabic, tragacanth gum, galactan, carob gum, guar gum, karaya gum, carrageenan, pectin, agar, quince seed (marmelo), starch (from rice, corn, potato or wheat and the like), algae colloids, trant gum and locust bean gum, microbial polymers such as xanthan gum, dextran, succinoglycan and pullulan, animal-based polymers such as collagen, casein, albumin and gelatin, starch-based polymers such as carboxymethyl starch and methylhydroxypropyl starch, cellulose-based polymers such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose and cellulose powders, alginic acid-based polymers such as sodium alginate and propylene glycol alginate, vinyl-based polymer compounds such as polyvinyl methyl ether and carboxyvinyl polymers, polyoxyethylene-based polymer compounds, polyoxyethylene-polyoxypropylene copolymer compounds, acrylic polymers such as sodium polyacrylate, polyethyl acrylate, polyacrylamide and acryloyldimethyl taurate copolymers, synthetic water-soluble polymers such as polyethyleneimine and cation polymers, and inorganic water-soluble polymers such as bentonite, aluminum magnesium silicate, montmorillonite, beidellite, nontronite, saponite, hectorite and anhydrous silicic acid. The blend amount of these polymers is preferably within a range from 0.1 to 25% by mass of the entire cosmetic material.

Depending on the intended purpose, the cosmetic material of the present invention may also include one or more powders. Any powder typically used in conventional cosmetic materials may be used, regardless of the shape of the powder particles (spherical, needle-like or plate-like or the like), the particle size (fumed, microparticulate, pigment-grade or the like) or the particle structure (porous, or non-porous or the like). Examples of powders that may be used include inorganic powders, organic powders, surfactant metal salt powders, colored pigments, pearl pigments, metal powder pigments and natural colorants and the like. Specific examples include inorganic powders such as titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, anhydrous silicic acid, aluminum silicate, magnesium silicate, aluminum magnesium silicate, calcium silicate, barium silicate, strontium silicate, metal tungstenate salts, hydroxyapatite, vermiculite, higilite, bentonite, montmorillonite, hectorite, zeolite, ceramic powder, dicalcium phosphate, alumina, aluminum hydroxide, boron nitride and silica; organic powders such as polyamide powders, polyester powders, polyethylene powders, polypropylene powders, polystyrene powders, polyurethane powders, benzoguanamine powders, polymethylbenzoguanamine powders, tetrafluoroethylene powders, polymethylmethacrylate powders, cellulose powders, silk powders, nylon powders, 12-nylon and 6-nylon powders, silicone powders, as well as powders of styrene/acrylic acid copolymers, divinylbenzene/styrene copolymers, vinyl resins, urea resins, phenol resins, fluororesins, silicon resins, acrylic resins, melamine resins, epoxy resins, polycarbonate resins, and microcrystalline fiber powders, starch powders and lauroyl lysine powders; surfactant metal salt powders (metal soaps) such as zinc stearate, aluminum stearate, calcium stearate, magnesium stearate, zinc myristate, magnesium myristate, zinc cetylphosphate, calcium cetylphosphate and zinc sodium cetylphosphate; colored pigments including inorganic red pigments such as such as iron oxide, iron hydroxide and iron titanate, inorganic brown pigments such as γ-iron oxide, inorganic yellow pigments such as iron oxide yellow and yellow ocher, inorganic black pigments such as iron oxide black and carbon black, inorganic violet pigments such as manganese violet and cobalt violet, inorganic green pigments such as chromium hydroxide, chromium oxide, cobalt oxide and cobalt titanate, inorganic blue pigments such as Prussian blue and ultramarine blue, and synthetic resin powders such as lakes of tar-based colorants, lakes of natural dyes and synthetic resin powders prepared by complexing these powders; pearl pigments such as titanium oxide-coated mica, bismuth oxychloride, titanium oxide-coated bismuth oxychloride, titanium oxide-coated talc, dew pearl and titanium oxide-coated colored mica; metal powder pigments such as aluminum powder, copper powder and stainless steel powder; tar colorants such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; and natural colorants such as carminic acid, laccaic acid, carthamin, brazilin and crocin.

These powders may also be complexed, or treated with a typical oil agent, silicone oil, fluorine compound or surfactant or the like, provided the effects of the present invention are not impaired. Specifically, one or more powders treated with hydrolyzable silyl groups or alkyl groups having a hydrogen atom bonded directly to a silicon atom, linear and/or branched organopolysiloxanes having hydrolyzable silyl groups or hydrogen atoms bonded directly to silicon atoms, linear and/or branched organopolysiloxanes having hydrolyzable silyl groups or hydrogen atoms bonded directly to silicon atoms that have also been co-modified with long-chain alkyl groups, linear and/or branched organopolysiloxanes having hydrolyzable silyl groups or hydrogen atoms bonded directly to silicon atoms that have also been co-modified with a polyoxyalkylene, and acrylic-silicone-based copolymers having hydrolyzable silyl groups or hydrogen atoms bonded directly to silicon atoms may also be used.

Further, the blend amount of the powder is preferably within a range from 0.1 to 99% by mass of the entire cosmetic material. In the case of a powered solid cosmetic material, the blend amount of the powder is preferably within a range from 80 to 99% by mass of the entire cosmetic material.

Depending on the intended purpose, the cosmetic material of the present invention may also employ one or more surfactants. These surfactants may be anionic, cationic, nonionic or amphoteric surfactants, and any of the surfactants used in conventional cosmetic materials may be used without any particular restriction.

Specific examples of anionic surfactants include fatty acid soaps such as sodium stearate and triethanolamine palmitate, alkyl ether carboxylic acids and salts thereof, salts of condensates of amino acids and fatty acids, alkane sulfonates, alkene sulfonates, sulfonates of fatty acid esters, sulfonates of fatty acid amides, sulfonates of formalin condensates, salts of alkyl sulfate esters, salts of secondary higher alcohol sulfate esters, salts of alkyl and aryl ether sulfate esters, salts of fatty acid ester sulfates, salts of fatty acid alkylolamide sulfate esters, salts of sulfate esters such as salts of Turkey red oil, alkyl phosphate salts, ether phosphate salts, alkyl allyl ether phosphate salts, amide phosphate salts, N-acyl lactate salts, N-acyl sarcosinate salts, and N-acyl amino acid-based surfactants.

Specific examples of the cationic surfactants include amine salts such as alkylamine salts, polyamines and amino alcohol fatty acid derivatives, as well as alkyl-based quaternary ammonium salts, aromatic quaternary ammonium salts, pyridinium salts and imidazolium salts.

Specific examples of the nonionic surfactants include sorbitan fatty acid esters, glycerol fatty acid esters, polyglycerol fatty acid esters, propylene glycol fatty acid esters, polyethylene glycol fatty acid esters, sucrose fatty acid esters, methyl glucoside fatty acid esters, alkyl polyglucosides, polyoxyethylene alkyl ethers, polyoxypropylene alkyl ethers, polyoxyethylene alkylphenyl ethers, polyoxyethylene fatty acid esters, polyoxyethylene sorbitan fatty acid esters, polyoxyethylene sorbitol fatty acid esters, polyoxyethylene glycerol fatty acid esters, polyoxyethylene propylene glycol fatty acid esters, polyoxyethylene castor oil, polyoxyethylene hardened castor oil, polyoxyethylene phytostanol ethers, polyoxyethylene phytosterol ethers, polyoxyethylene cholestanol ethers, polyoxyethylene cholesteryl ethers, linear or branched polyoxyalkylene-modified organopolysiloxanes, linear or branched polyoxyalkylene/alkyl-comodified organopolysiloxanes, linear or branched polyglycerol-modified organopolysiloxanes, linear or branched polyglycerol/alkyl-comodified organopolysiloxanes, alkanolamides, sugar ethers and sugar amides.

Specific examples of the amphoteric surfactants include betaine, phosphatidylcholine, aminocarboxylates, imidazoline derivatives and amide amines. Of these surfactants, linear or branched organopolysiloxanes having a polyoxyalkylene chain or polyglycerol chain within the molecule, and linear or branched organopolysiloxanes that also contain long-chain alkyl groups of 6 to 20 carbon atoms are preferred.

Further, in these surfactants, the amount of hydrophilic polyoxyalkylene groups or polyglycerol residues preferably represents 10 to 70% by mass of the molecule, and the blend amount of the surfactant is typically within a range from 0.1 to 20% by mass, and preferably 0.2 to 10% by mass, of the entire cosmetic material.

The cosmetic material of the present invention may also include a silicone resin selected from amongst acrylic silicone resins and network-type silicone resins. Acrylic silicone resins include acrylic/silicone graft and block copolymers. Further, acrylic silicone resins containing one or more groups selected from among a pyrrolidinyl group, long-chain alkyl groups, polyoxyalkylene groups, and anionic groups such as fluoroalkyl groups and carboxyl groups within the resin molecule may also be used.

Network-type silicone resins may be selected from resins composed of $R^1{}_3SiO_{0.5}$ units and $SiO_2$ units, resins composed of $R^1{}_3SiO_{0.5}$ units, $R^1{}_2SiO$ units and $SiO_2$ units, resins composed of $R^1{}_3SiO_{0.5}$ units and $R^1SiO_{1.5}$ units, resins composed of $R^1_3SiO_{0.5}$ units, $R^1_2SiO$ units and $R^1SiO_{1.5}$ units, and resins composed of $R^1_3SiO_{0.5}$ units, $R^1_2SiO$ units, $R^1SiO_{1.5}$ units and $SiO_2$ units. Further, network-type silicone resins containing one or more groups selected from among a pyrrolidinyl group, long-chain alkyl groups, polyoxyalkylene groups, fluoroalkyl groups and amino groups within the resin molecule may also be used. When used, the blend amount of the silicone resin is preferably within a range from 0.1 to 20% by mass, and preferably from 1 to 10% by mass, relative to the total mass of the cosmetic material.

The cosmetic material of the present invention may use a composition composed of one or more cross-linked organopolysiloxanes and one or more oils agents that are liquid at room temperature, which are selected in accordance with the intended purpose of the material. The cross-linked organopolysiloxane preferably undergoes swelling by incorporating more than its own mass of the liquid oil agent. Examples of liquid oils that may be used include the liquid silicone oils, hydrocarbon oils, ester oils, natural animal-based and plant-based oils, synthetic oils and fluorine-based oils described above. Specific examples include low-viscosity silicone oils having a viscosity of 0.65 to 100.0 mm²/s (25° C.), hydrocarbon oils such as liquid paraffin, squalane, isododecane and isohexadecane, glyceride oils such as trioctanoin, ester oils such as isotridecyl isononanoate, N-acylglutamate esters, and lauroyl sarcosinate esters, and natural animal-based or plant-based oils such as macadamia nut oil. Furthermore, the cross-linking agent for these cross-linked organopolysiloxanes is preferably a compound having two or more vinylic reactive sites within each molecule, which form cross-linked structures by reacting with hydrogen atoms bonded directly to silicon atoms. Examples of this compound having two or more vinylic reactive sites within each molecule include organopolysiloxanes having two or more vinyl groups within each molecule, polyoxyalkylenes having two or more allyl groups within each molecule, polyglycerols having two or more allyl groups within each molecule, and α,ω-alkenyldienes. Furthermore, cross-linking agents containing at least one group selected from the group consisting of polyoxyalkylene groups, polyglycerol residues, long-chain alkyl groups, alkenyl groups, aryl groups and fluoroalkyl groups may also be used. In those cases where a composition composed of a cross-linked organopolysiloxane and an oil agent that is liquid at room temperature is used, the blend amount of the composition is preferably within a range from 0.1 to 80% by mass, and more preferably from 1 to 50% by mass, of the total mass of the cosmetic material.

Depending on the intended purpose, the cosmetic material of the present invention may also incorporate a silicone-modified olefin wax obtained by subjecting a unsaturated group-containing olefin wax, obtained by reacting one or more α-olefins with a diene, and an organohydrogenpolysiloxane having one or more SiH bonds within each molecule to an addition reaction. The α-olefin is preferably an α-olefin of 2 to 12 carbon atoms such as ethylene, propylene, 1-butene, 1-hexene or 4-methyl-1-pentene, and the diene is preferably butadiene, isoprene, 1,4-hexadiene, vinylnorbornene, ethylidene norbornene or dicyclopentadiene or the like. The organohydrogenpolysiloxane having one or more SiH bonds may have a linear structure or a branched structure.

Other additives may also be included within the cosmetic material of the present invention provided their inclusion does not impair the effects of the present invention, and examples of these additives include components used in conventional cosmetic materials, oil-soluble gelling agents, organic-modified clay minerals, antiperspirants, ultraviolet absorbers, ultraviolet absorption and scattering agents, moisturizers, preservatives, antibacterial agents, fragrances, salts, antioxidants, pH modifiers, chelating agents, algefacients, anti-inflammatory agents, skin beautifying components (such as whitening agents, cell activators, rough skin improvers, blood circulation promoters, skin astringents and anti-seborrheic agents), vitamins, amino acids, nucleic acids, hormones, clathrate compounds and hair-setting agents.

Specific examples of the oil-based gelling agents include those selected from among metal soaps such as aluminum stearate, magnesium stearate and zinc myristate, amino acid derivatives such as N-lauroyl-L-glutamic acid and α,γ-di-n-butylamine, dextrin fatty acid esters such as dextrin palmitate, dextrin stearate and dextrin 2-ethylhexanoate palmitate, sucrose fatty acid esters such as sucrose palmitate and sucrose stearate, fructooligosaccharide fatty acid esters such as fructooligosaccharide stearate and fructooligosaccharide 2-ethylhexanoate, benzylidene derivatives of sorbitol such as monobenzylidene sorbitol and dibenzylidene sorbitol, and organic-modified clay minerals such as dimethylbenzyldodecylammonium montmorillonite clay and dimethyldioctadecylammonium montmorillonite clay.

Specific examples of the antiperspirants include those selected from among aluminum chlorohydrate, aluminum chloride, aluminum sesquichlorohydrate, zirconyl hydroxychloride, aluminum zirconium hydroxychloride, and aluminum zirconium glycine complex.

Specific examples of the ultraviolet absorbers include benzoic acid-based ultraviolet absorbers such as para-aminobenzoic acid, anthranilic acid-based ultraviolet absorbers such as methyl anthranilate, salicylic acid-based ultraviolet absorbers such as methyl salicylate, octyl salicylate and trimethylcyclohexyl salicylate, cinnamic acid-based ultraviolet absorbers such as octyl para-methoxycinnamate, benzophenone-based ultraviolet absorbers such as 2,4-dihydroxybenzophenone, urocanic acid-based ultraviolet absorbers such as ethyl urocanate, dibenzoylmethane-based ultraviolet absorbers such as 4-t-butyl-4'-methoxy-dibenzoylmethane, as well as phenylbenzimidazole sulfonic acid and triazine derivatives. Specific examples of the ultraviolet absorption and scattering agents include powders that are capable of absorbing and scattering ultraviolet light, such as microparticulate titanium oxide, microparticulate iron-containing titanium oxide, microparticulate zinc oxide, microparticulate cerium oxide, and complexes thereof. A dispersion prepared in advance by dispersing these types of powders capable of absorbing and scattering ultraviolet light in an oil agent may also be used.

Specific examples of the moisturizers include glycerol, sorbitol, propylene glycol, dipropylene glycol, 1,3-butylene glycol, pentylene glycol, glucose, xylitol, maltitol, polyethylene glycol, hyaluronan, chondroitin sulfate, pyrrolidone carboxylate, polyoxyethylene methyl glucoside, polyoxypropylene methyl glucoside, egg yolk lecithin, soybean lecithin, phosphatidylcholine, phosphatidylethanolamine, phosphatidylserine, phosphatidylglycerol, phosphatidylinositol and sphingophospholipid.

Specific examples of the preservatives include alkyl paraoxybenzoates, benzoic acid, sodium benzoate, sorbic acid, potassium sorbate and phenoxyethanol, whereas specific examples of the antibacterial agents include benzoic acid, salicylic acid, carbolic acid, sorbic acid, alkyl paraoxybenzoates, parachlorometacresol, hexachlorophene, benzalkonium chloride, chlorhexidine chloride, trichlorocarbanilide, photosensitizers and phenoxyethanol.

Examples of the salts include inorganic salts, organic acid salts, amine salts and salts of amino acids. Specific examples of the inorganic salts include the sodium salts, potassium salts, magnesium salts, calcium salts, aluminum salts, zirconium salts and zinc salts of inorganic acid such as hydrochloric acid, sulfuric acid, carbonic acid and nitric acid. Specific examples of the organic acid salts include salts of organic acids such as acetic acid, dehydroacetic acid, citric acid, malic acid, succinic acid, ascorbic acid and stearic acid. Specific examples of the amine salts and amino acid salts include salts of amines such as triethanolamine and salts of amino acids such as glutamic acid. Other salts that may be used include salts of hyaluronic acid and chondroitin sulfuric acid, aluminum zirconium glycine complexes, and salts produced by acid-alkaline neutralization within the cosmetic formulation.

Specific examples of the antioxidants include tocopherol, p-t-butylphenol, butylhydroxyanisole, dibutylhydroxytoluene and phytic acid, specific examples of the pH modifiers include lactic acid, citric acid, glycolic acid, succinic acid, tartaric acid, dl-malic acid, potassium carbonate, sodium hydrogen carbonate and ammonium hydrogen carbonate, specific examples of the chelating agents include alanine, sodium ethylenediamine tetraacetate, sodium polyphosphate, sodium metaphosphate and phosphoric acid, specific examples of the algefacients include L-menthol and camphor, and specific examples of the anti-inflammatory agents include allantoin, glycyrrhizinic acid and salts thereof, glycyrrhetinic acid and stearyl glycyrrhetinate, tranexamic acid and azulene.

Specific examples of the skin beautifying components include whitening agents such as placenta extract, arbutin, glutathione and Yukinoshita extract, cell activators such as royal jelly, photosensitizers, cholesterol derivatives and calf blood extract, rough skin improvers, blood circulation promoters such as nonylic acid vanillylamide, benzyl nicotinate, β-butoxyethyl nicotinate, capsaicin, zingerone, cantharis tincture, ichthammol, caffeine, tannic acid, α-borneol, tocopherol nicotinate, inositol hexanicotinate, cyclandelate, cinnarizine, tolazoline, acetylcholine, verapamil, cepharanthine and γ-orizanol, skin astringents such as zinc oxide and tannic acid, and anti-seborrheic agents such as sulfur and thianthol.

Specific examples of the vitamins include A vitamins such as vitamin A oil, retinol, retinol acetate and retinol palmitate, B vitamins, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and derivatives thereof, and vitamin $B_{15}$ and derivatives thereof, C vitamins such as L-ascorbic acid, L-ascorbic acid dipalmitic ester, sodium L-ascorbate-2-sulfate and dipotassium L-ascorbic acid diphosphate, D vitamins such as ergocalciferol and cholecalciferol, E vitamins such as α-tocopherol, —-tocopherol, γ-tocopherol, dl-α-tocopherol acetate, dl-α-tocopherol nicotinate and dl-α-tocopherol succinate, vitamin H, vitamin P, nicotinic acids such as nicotinic acid, benzyl nicotinate and nicotinic acid amide, pantothenic acids such as calcium pantothenate, D-pantothenyl alcohol, pantothenyl ethyl ether and acetylpantothenyl ethyl ether, and biotin.

Specific examples of the amino acids include glycine, valine, leucine, isoleucine, serine, threonine, phenylalanine, alginine, lysine, aspartic acid, glutamic acid, cystine, cysteine, methionine and tryptophan, a specific example of the nucleic acids is deoxyribonucleic acid, and specific examples of the hormones include estradiol and ethenylestradiol.

Examples of hair-setting polymer compounds include amphoteric, anionic, cationic and nonionic polymer compounds, including polyvinylpyrrolidone-based polymers such as polyvinylpyrrolidone and vinylpyrrolidone/vinyl acetate copolymers, acidic vinyl ether-based polymer compounds such as methyl vinyl ether/maleic anhydride alkyl half-ester copolymers, acidic polyvinyl acetate-based polymer compounds such as vinyl acetate/crotonic acid copolymers, acidic acrylic polymer compounds such as (meth)acrylic acid/alkyl (meth)acrylate copolymers and (meth)acrylic acid/alkyl (meth)acrylate/alkyl acrylamide copolymers, and amphoteric acrylic polymer compounds such as N-methacryloylethyl-N,N-dimethylammonium α-N-methylcarboxybetaine/alkyl (meth)acrylate copolymers and hydroxypropyl (meth)acrylate/butylaminoethyl methacrylate/octylamide acrylate copolymers. Furthermore, naturally derived polymer compounds such as cellulose or derivatives thereof, keratin or derivatives thereof, and collagen or derivatives thereof can also be used favorably.

In the present invention, there are no particular restrictions on the formulation or form of the cosmetic material, and examples of the cosmetic material include water-based liquids such as cosmetic washes, oil-based liquids such as cleansing oils, water-based and oil-based emulsions including water-in-oil (W/O) emulsions, oil-in-water (O/W) emulsions, non-aqueous emulsions, W/O/W and O/W/O emulsions, such as lotions, creams, cream foundations and massage oils, as well as paste-like formulations such as makeup foundations and concealers, and solid formulations such as powder foundations, eye shadows, and packs.

There are also no particular restrictions on applications of the cosmetic material. Examples of possible applications include skin care cosmetic material such as cosmetic washes, lotions, creams, cleansing materials, packs, oil liquids, massage formulations, beauty lotions, beauty oils, hand creams, lip creams and wrinkle concealers; cosmetic makeup materials such as makeup foundations, concealers, whitening powders, powder foundations, liquid foundations, cream foundations, oil-based foundations, blushers, eye shadows, mascaras, eye liners, eyebrow materials and lipsticks; hair cosmetic materials such as shampoos, conditioners, treatments and setting agents; ultraviolet protection cosmetic materials such as sunblock oils, sunblock lotions and sunblock creams; as well as cleansers, deodorants and antiperspirants and the like.

EXAMPLES

The present invention is described in more detail below using a series of examples, although the present invention is in no way limited by the examples presented below.

Example 1

A reaction container was charged with 234 parts by mass of an organohydrogenpolysiloxane represented by formula (10) shown below,

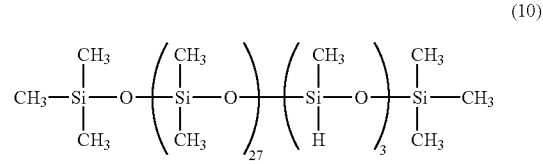

(10)

44.1 parts by mass of allylsuccinic anhydride represented by formula (11) shown below,

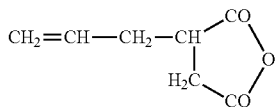
(11)

and 100 parts by mass of toluene, and following the addition of 0.1 parts of a 0.5% by mass toluene solution of chloroplatinic acid, the resulting mixture was reacted for 2 hours under reflux. The toluene was then removed by distillation by heating the reaction product under reduced pressure, yielding an acid anhydride group-containing organopolysiloxane represented by formula (12) shown below.

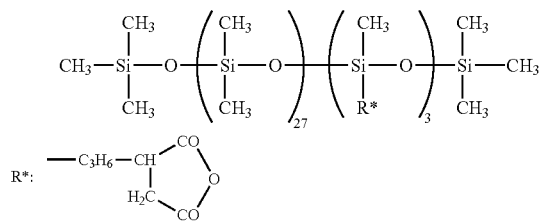
(12)

To 250 parts by mass of this acid anhydride group-containing organopolysiloxane were added 100 parts by mass of tetrahydrofuran and 24.7 parts by mass of 2-amino-1,3-propanediol, and the resulting mixture was reacted for 2 hours under reflux. The solvent was then removed from the reaction product by distillation under reduced pressure, yielding a carboxyl group-containing organopolysiloxane represented by formula (13) shown below.

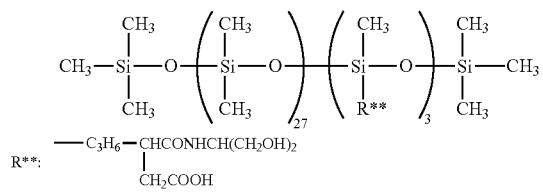
(13)

Example 2

A reaction container was charged with 241 parts by mass of an organohydrogenpolysiloxane represented by formula (14) shown below,

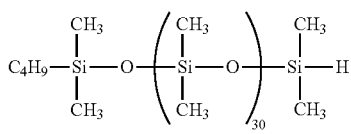
(14)

14.7 parts by mass of allylsuccinic anhydride represented by formula (11) above, and 100 parts by mass of toluene, and following the addition of 0.1 parts of a 0.5% by mass toluene solution of chloroplatinic acid, the resulting mixture was reacted for 2 hours under reflux. The solvent was then removed by distillation by heating the reaction product under reduced pressure, yielding an acid anhydride group-containing organopolysiloxane represented by formula (15) shown below.

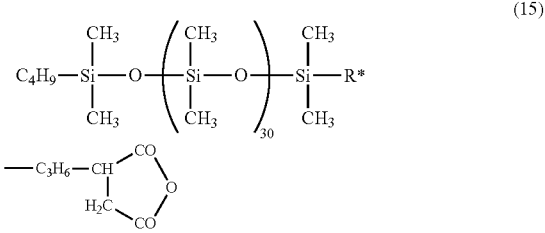
(15)

To 255 parts by mass of this acid anhydride group-containing organopolysiloxane were added 100 parts by mass of tetrahydrofuran and 9.1 parts by mass of 2-amino-1,3-propanediol, and the resulting mixture was reacted for 2 hours under reflux. The solvent was then removed from the reaction product by distillation under reduced pressure, yielding a carboxyl group-containing organopolysiloxane represented by formula (16) shown below.

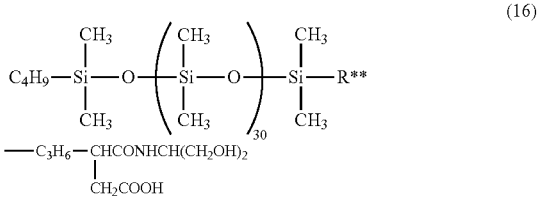
(16)

Example 3

A reaction container was charged with 266 parts by mass of an organohydrogenpolysiloxane represented by formula (17) shown below,

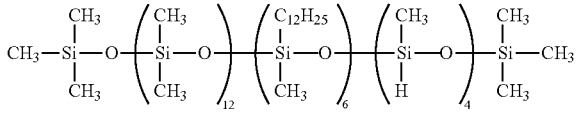
(17)

58.8 parts by mass of allylsuccinic anhydride represented by formula (11) above, and 100 parts by mass of toluene, and following the addition of 0.1 parts of a 0.5% by mass toluene solution of chloroplatinic acid, the resulting mixture was reacted for 2 hours under reflux. The solvent was then removed by distillation by heating the reaction product under reduced pressure, yielding an acid anhydride group-containing organopolysiloxane represented by formula (18) shown below.

(18)

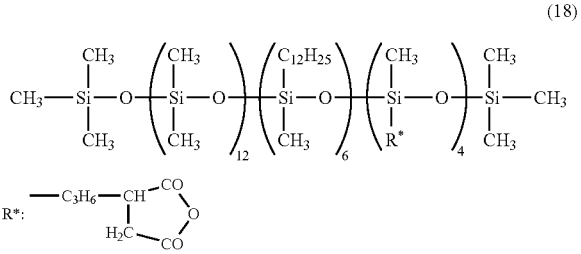

To 250 parts by mass of this acid anhydride group-containing organopolysiloxane were added 100 parts by mass of tetrahydrofuran and 33 parts by mass of diethanolamine, and the resulting mixture was reacted for 2 hours under reflux. The solvent was then removed from the reaction product by distillation under reduced pressure, yielding a carboxyl group-containing organopolysiloxane represented by formula (19) shown below.

(19)

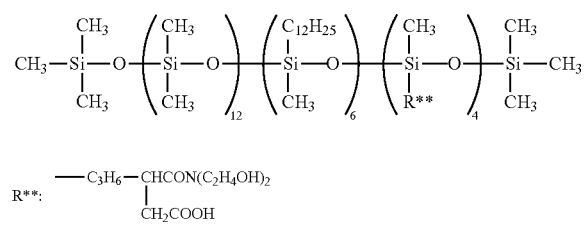

Example 4

A reaction container was charged with 240 parts by mass of an organohydrogenpolysiloxane represented by formula (20) shown below, (20)

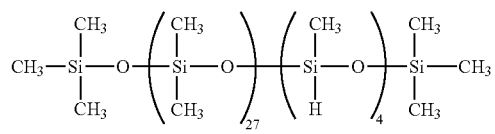

28.0 parts by mass of allylsuccinic anhydride represented by formula (11) above, 168 parts by mass of an organopolysiloxane having a vinyl group at one terminal, represented by formula (21) shown below, (21)

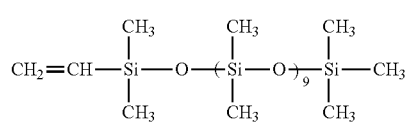

and 100 parts by mass of toluene, and following the addition of 0.1 parts of a 0.5% by mass toluene solution of chloroplatinic acid, the resulting mixture was reacted for 2 hours under reflux. The solvent was then removed by distillation by heating the reaction product under reduced pressure, yielding an acid anhydride group-containing organopolysiloxane represented by formula (22) shown below.

(22)

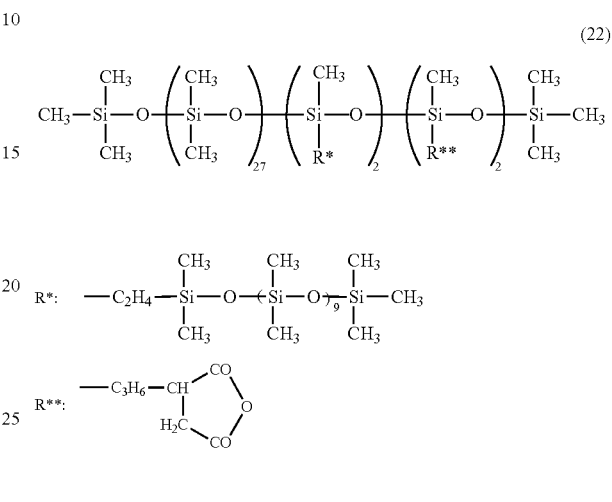

To 250 parts by mass of this acid anhydride group-containing organopolysiloxane were added 100 parts by mass of tetrahydrofuran and 10.5 parts by mass of 2-amino-1,3-propanediol, and the resulting mixture was reacted for 5 hours under reflux. The solvent was then removed from the reaction product by distillation under reduced pressure, yielding a carboxyl group-containing organopolysiloxane represented by formula (23) shown below.

(23)

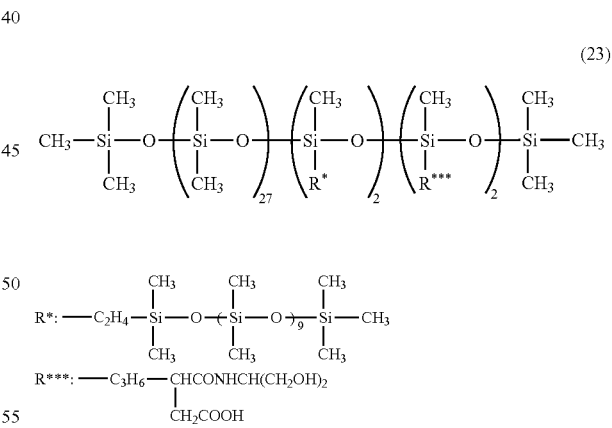

Examples 5 to 8, Comparative Examples 1 and 2

Using the organopolysiloxanes obtained in examples 1 to 4, oil-based foundations having the formulations (units: parts by mass) shown in the following table were prepared and evaluated.

TABLE 1

| | | Example | | | | Comparative example | |
|---|---|---|---|---|---|---|---|
| | Component | 5 | 6 | 7 | 8 | 1 | 2 |
| 1 | Starch fatty acid ester | 6.0 | 6.0 | 6.0 | 6.0 | 6.0 | 6.0 |
| 2 | Ceresin | 7.0 | 7.0 | 7.0 | 7.0 | 7.0 | 7.0 |
| 3 | Polybutene | 4.0 | 4.0 | 4.0 | 4.0 | 4.0 | 4.0 |
| 4 | Liquid paraffin | 34.0 | 34.0 | 34.0 | 34.0 | 34.0 | 34.0 |
| 5 | The organopolysiloxane of example 1 | 6.0 | — | — | — | — | — |
| 6 | The organopolysiloxane of example 2 | — | 6.0 | — | — | — | — |
| 7 | The organopolysiloxane of example 3 | — | — | 6.0 | — | — | — |
| 8 | The organopolysiloxane of example 4 | — | — | — | 6.0 | — | — |
| 9 | Polyglycerol-modified silicone (note 1) | — | — | — | — | 6.0 | — |
| 10 | Polysiloxane (note 2) | — | — | — | — | — | 6.0 |
| 11 | Titanium oxide | 33.0 | 33.0 | 33.0 | 33.0 | 33.0 | 33.0 |
| 12 | Titanated mica | 3.0 | 3.0 | 3.0 | 3.0 | 3.0 | 3.0 |
| 13 | Colored pigment | 7.0 | 7.0 | 7.0 | 7.0 | 7.0 | 7.0 |
| 14 | Preservative | suitable amount | suitable amount | suitable amount | suitable amount | suitable amount | suitable amount |
| 15 | Fragrance | suitable amount | suitable amount | suitable amount | suitable amount | suitable amount | suitable amount |

(note 1) KF-6105, manufactured by Shin-Etsu Chemical Co., Ltd.
(note 2) The polysiloxane represented by the formula below.

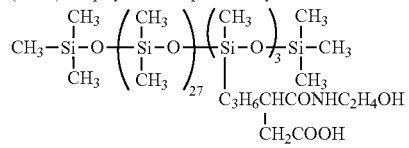

(Production Method)
A: Components 1 to 10 were heated and melted.
B: Components 11 to 15 were mixed with the melt obtained in A.
C: The mixture from B was dispersed uniformly using a triple roll mill
D: The mixture from C was heated and melted, and following defoaming, was poured into a metal mold and cooled.

The thus obtained foundations were subjected to actual usage tests by 50 specialist female panelists, and the skin adhesion, spreadability, uniformity of the cosmetic film and cosmetic retention were each evaluated against the criteria listed below.

[Evaluation Criteria]
5 points: Very good
4 points: Good
3 points: Fair
2 points: Slightly poor
1 point: Poor For each evaluated property, the average number of points across all the panelists was recorded. In Table 2, the meanings of the grades awarded are as listed below.
Average number of points:
4.5 points or higher: A
At least 3.5 points but less than 4.5 points: B
At least 2.5 points but less than 3.5 points: C
At least 1.5 points but less than 2.5 points: D
Less than 1.5 points: E

TABLE 2

| | Example 5 | Example 6 | Example 7 | Example 8 | Comparative example 1 | Comparative example 2 |
|---|---|---|---|---|---|---|
| Skin adhesion | B | A | A | A | B | B |
| Spreadability | A | B | B | B | B | C |
| Cosmetic film uniformity | A | A | A | A | B | B |
| Cosmetic retention | A | A | A | A | C | C |

As illustrated in Table 2, comparative examples 1 and 2 suffered from poor pigment dispersibility, and the spreadability and cosmetic retention were also inferior. In contrast, in the foundations of examples 5 to 8, the pigment was finely dispersed, the spreadability felt light, the skin adhesion was excellent, and the cosmetic film was uniform and exhibited good retention.

Examples 9 and 10, Comparative Examples 3 and 4

Using the organopolysiloxanes obtained in examples 1 and 2, W/O foundations having the formulations (units: parts by mass) shown in the following table were prepared and evaluated.

TABLE 3

| Component | Example 9 | Example 10 | Comparative example 3 | Comparative example 4 |
|---|---|---|---|---|
| 1 Decamethylcyclopentasiloxane | 45.0 | 45.0 | 45.0 | 45.0 |
| 2 Dimethylpolysiloxane | 5.0 | 5.0 | 5.0 | 5.0 |
| 3 The organopolysiloxane of example 1 | 2.0 | — | — | — |
| 4 The organopolysiloxane of example 2 | — | 2.0 | — | — |
| 5 Polyglycerol-modified silicone(note 1) | — | — | 2.0 | — |
| 6 Polysiloxane(note 2) | — | — | — | 2.0 |
| 7 Octadecyldimethylbenzylammonium salt-modified montmorillonite | 4.0 | 4.0 | 4.0 | 4.0 |
| 8 Hydrophobically treated titanium oxide(note 3) | 10.0 | 10.0 | 10.0 | 10.0 |
| 9 Hydrophobically treated talc(note 3) | 6.0 | 6.0 | 6.0 | 6.0 |
| 10 Hydrophobically treated mica(note 3) | 6.0 | 6.0 | 6.0 | 6.0 |
| 11 Hydrophobically treated red iron oxide(note 3) | 1.6 | 1.6 | 1.6 | 1.6 |
| 12 Hydrophobically treated yellow iron oxide(note 3) | 0.7 | 0.7 | 0.7 | 0.7 |
| 13 Hydrophobically treated black iron oxide(note 3) | 0.2 | 0.2 | 0.2 | 0.2 |
| 14 Dipropylene glycol | 5.0 | 5.0 | 5.0 | 5.0 |
| 15 Methyl paraoxybenzoate | 0.3 | 0.3 | 0.3 | 0.3 |
| 16 Fragrance | suitable amount | suitable amount | suitable amount | suitable amount |
| 17 Water | remainder | remainder | remainder | remainder |

(note 1) and (note 2) are as described above for (note 1) and (note 2) of examples 5 to 8 and comparative examples 1 and 2.
(note 3) 2% of methylhydrogenpolysiloxane was added relative to the mass of the powder, and a heat treatment was then performed at 150° C.

(Production Method)

A: Components 1 to 7 were mixed under heat, and components 8 to 13 were then added and stirred to obtain a uniform mixture.

B: Components 14 and 15 were dissolved in component 17 under heat.

C: Under constant stirring, the solution obtained in B was added gradually to the mixture obtained in A and emulsified. The resulting emulsion was cooled, and component 16 was added to complete the preparation of a foundation.

The thus obtained foundations were subjected to actual usage tests by 50 specialist female panelists in the same manner as that described for examples 5 to 8.

TABLE 4

|  | Example 9 | Example 10 | Comparative example 3 | Comparative example 4 |
|---|---|---|---|---|
| Skin adhesion | B | A | B | C |
| Spreadability | A | B | B | C |
| Cosmetic film uniformity | A | A | B | B |
| Cosmetic retention | A | A | C | B |

As is evident from the above table, compared with the foundations of comparative examples 3 and 4, the foundations of examples 9 and 10 exhibited a more uniform cosmetic film, and displayed better cosmetic retention. Further, the foundation of comparative example 4 suffered from poor emulsion properties, and also exhibited poor stability over time, with the foundation undergoing phase separation.

In the following examples, stability over time was evaluated by placing the cosmetic material in a sealed container, leaving the container to stand for one month at 50° C., and then checking that the material had undergone no change in external appearance. Furthermore, in the following description, "%" represents "% by mass".

Example 11

Eye Liner

| (Components) | (%) |
|---|---|
| 1. Octamethylcyclotetrasiloxane | remainder |
| 2. The organopolysiloxane of example 2 | 3.0 |
| 3. Silicone resin (note 1) | 15.0 |
| 4. Dioctadecyldimethylammonium salt-modified montmorillonite | 3.0 |
| 5. Silicone-treated black iron oxide (note 2) | 10.0 |
| 6. 1,3-butylene glycol | 5.0 |
| 7. Preservative | appropriate amount |
| 8. Fragrance | appropriate amount |
| 9. Pure water | 10.0 |

(note 1) Silicone resin: A 50%-D5 solution of a silicone network compound having a $[Me_3SiO_{1/2}]/[SiO_2]$ ratio of 0.8
(note 2) Silicone-treated black iron oxide: 2% by mass of methylhydrogenpolysiloxane was added relative to the mass of black iron oxide, and the resulting mixture was heat treated at 150° C.

(Production Method)

A: Components 1 to 4 were mixed, and component 5 was then added and dispersed uniformly by mixing.

B: Components 6 to 8 were mixed together.

C: The mixture obtained in B was added gradually to the dispersion obtained in A and emulsified, and component 9 was then added to complete preparation of an eye liner.

The eye liner obtained in this manner was readily spread and easy to draw, suffered no stickiness, underwent no change upon temperature variation and no change over time, and also exhibited extremely favorable cosmetic retention.

Example 12

Suntan Lotion

| (Components) | (%) |
| --- | --- |
| 1. Emulsifying composition (note 1) | 6.0 |
| 2. Dimethylpolysiloxane (20 cs) | 49.0 |
| 3. 1,3-butylene glycol | 5.0 |
| 4. Sodium dehydroacetate | appropriate amount |
| 5. Antioxidant | appropriate amount |
| 6. Preservative | appropriate amount |
| 7. Fragrance | appropriate amount |
| 8. Pure water | remainder |

(note 1) Emulsifying composition: a composition consisting of components a to c listed below:
a: the organopolysiloxane of example 3, 10.0 parts by mass
b: dioctadecyldimethylammonium salt-modified montmorillonite, 10.0 parts by mass
c: ethanol, 40.0 parts by mass (Production Method)
A: Component a was dissolved in component c, and component b was added.
B: The mixture from A was stirred for one hour using a disper, and the ethanol was removed using an evaporator.
C: The mixture obtained in B was dried for a full day at 50° C., yielding the emulsifying composition of component 1.
D: The component 1 obtained in C was mixed with component 2.
E: Components 3 to 6 and component 8 were mixed together uniformly.
F: Under constant stiffing, the mixture obtained in E was added gradually to the mixture obtained in D and emulsified, and component 7 was then added to complete preparation of a suntan lotion.

The suntan lotion obtained in this manner had a fine texture, was readily spread, suffered no stickiness or greasiness, imparted a fresh feeling upon use, and underwent no change over time.

Example 13

Suntan Cream

| (Components) | (%) |
| --- | --- |
| 1. Decamethylcyclopentasiloxane | 15.0 |
| 2. Dimethylpolysiloxane (100 cs) | 5.0 |
| 3. Silicone wax | 0.5 |
| 4. The organopolysiloxane of example 4 | 6.0 |
| 5. Palmitic acid | 0.2 |
| 6. Dimethyloctyl-para-aminobenzoic acid | 0.5 |
| 7. 4-t-butyl-4'-methoxy-dibenzoylmethane | 0.5 |
| 8. Kaolin | 0.5 |
| 9. Red iron oxide | 0.2 |
| 10. Yellow iron oxide | 0.3 |
| 11. Black iron oxide | 0.1 |
| 12. Titanium oxide-coated mica | 1.0 |
| 13. Sodium L-glutamate | 3.0 |
| 14. 1,3-butylene glycol | 5.0 |
| 15. Dioctadecyldimethylammonium chloride | 0.1 |
| 16. Antioxidant | appropriate amount |
| 17. Preservative | appropriate amount |
| 18. Fragrance | appropriate amount |
| 19. Pure water | remainder |

(Production Method)
A: Components 1 to 7 and components 16 to 17 were heated and dissolved.
B: Component 15 and a portion of component 19 were stirred under heat, and components 8 to 12 were added and dispersed.
C: Components 13 and 14 were dissolved in the remainder of component 19, and the resulting solution was mixed with the dispersion obtained in B.
D: Under constant stiffing, the dispersion obtained in C was added gradually to the mixture obtained in A and emulsified, the resulting emulsion was cooled, and component 18 was then added to complete preparation of a suntan cream.

The suntan cream obtained in this manner had a fine texture, was readily spread, suffered no stickiness, felt appropriately wet, imparted a fresh feeling upon use, and underwent no change over time. The cosmetic retention was also good.

Example 14

Hair Cream

| (Components) | (%) |
| --- | --- |
| 1. Decamethylcyclopentasiloxane | 10.0 |
| 2. Methylphenylpolysiloxane | 5.0 |
| 3. Squalane | 4.0 |
| 4. Silicone resin | 1.0 |
| 5. Glyceryl dioleate | 2.0 |
| 6. The organopolysiloxane of example 4 | 4.0 |
| 7. Sodium sorbitol sulfate | 2.0 |
| 8. Sodium chondroitin sulfate | 1.0 |
| 9. Sodium hyaluronate | 0.5 |
| 10. Propylene glycol | 3.0 |
| 11. Preservative | 1.5 |
| 12. Vitamin E acetate | 0.1 |
| 13. Antioxidant | appropriate amount |
| 14. Fragrance | appropriate amount |
| 15. Pure water | remainder |

(Production Method)
Silicone resin: A 50%-D5 solution of a silicone network compound having a $[Me_3SiO_{1/2}]/[SiO_2]$ ratio of 0.8
A: Components 1 to 6 and components 11 to 12 were mixed together under heat.
B: Components 7 to 10 were dissolved in component 15 under heat.
C: Under constant stirring, the solution obtained in B was added gradually to the mixture obtained in A and emulsified, the resulting emulsion was cooled, and component 14 was then added to complete preparation of a hair cream.

The hair cream obtained in this manner exhibited good spreadability, suffered no stickiness or greasiness, felt appropriately wet, imparted a fresh feeling upon use, and underwent no change over time.

Example 15

Eye Wrinkle Cream

| (Components) | (%) |
| --- | --- |
| 1. Decamethylcyclopentasiloxane | 20.0 |
| 2. Trimethylsiloxy silicate | 5.0 |

| (Components) | (%) |
| --- | --- |
| 3. The organopolysiloxane of example 3 | 5.0 |
| 4. Sodium chondroitin sulfate | 2.0 |
| 5. Sodium lactate | 1.0 |
| 6. Glycerol | 50.0 |
| 7. Preservative | appropriate amount |
| 8. Antioxidant | appropriate amount |
| 9. Fragrance | appropriate amount |
| 10. Pure water | remainder |

(Production Method)

A: Components 1 to 3 and component 8 were mixed together under heat.

B: Components 4 to 7 were dissolved in component 10 under heat.

C: Under constant stiffing, the solution obtained in B was added gradually to the mixture obtained in A and emulsified, the resulting emulsion was cooled, and component 9 was then added to complete preparation of an eye wrinkle cream.

The eye wrinkle cream in this manner exhibited good spreadability, suffered no stickiness or greasiness, felt appropriately wet, imparted a fresh feeling upon use, and underwent no change over time. The cosmetic retention was also good.

Example 16

Cream

| (Components) | (%) |
| --- | --- |
| 1. Decamethylcyclopentasiloxane | 20.0 |
| 2. Glyceryl trioctanoate | 10.0 |
| 3. The organopolysiloxane of example 1 | 4.0 |
| 4. Phenyldimethylstearylammonium chloride | 1.0 |
| 5. Dipropylene glycol | 10.0 |
| 6. Maltitol | 10.0 |
| 7. Saponite | 1.5 |
| 8. Preservative | appropriate amount |
| 9. Fragrance | appropriate amount |
| 10. Pure water | remainder |

(Production Method)

A: Components 1 to 4 and component 8 were mixed together under heat.

B: Components 5 to 7 were dissolved in component 10 under heat.

C: Under constant stiffing, the solution obtained in B was added gradually to the mixture obtained in A and emulsified, the resulting emulsion was cooled, and component 9 was then added to complete preparation of a cream.

The cream obtained in this manner exhibited good spreadability, suffered no stickiness or greasiness, felt appropriately wet, imparted a fresh feeling upon use, and underwent no change over time.

Example 17

Hand Cream

| (Components) | (%) |
| --- | --- |
| 1. Decamethylcyclopentasiloxane | 12.0 |
| 2. Liquid paraffin | 10.0 |
| 3. Organic silicone resin (note 1) | 5.0 |
| 4. The organopolysiloxane of example 4 | 4.0 |
| 5. Distearyldimethylammonium chloride | 0.8 |
| 6. Vitamin E acetate | 0.1 |
| 7. Polyethylene glycol 4000 | 1.0 |
| 8. Glycerol | 10.0 |
| 9. Aluminum magnesium silicate | 1.2 |
| 10. Preservative | appropriate amount |
| 11. Fragrance | appropriate amount |
| 12. Pure water | remainder |

(note 1) Organic silicone resin: average formula $(CH_3)_{1.60}SiO_{1.20}$, molecular weight: 3,000

(Production Method)

A: Components 1 to 6 and component 10 were mixed together under heat.

B: Components 7 to 9 were dissolved in component 12 under heat.

C: Under constant stiffing, the solution obtained in B was added gradually to the mixture obtained in A and emulsified, the resulting emulsion was cooled, and component 11 was then added to complete preparation of a hand cream.

The hand cream obtained in this manner exhibited good spreadability, suffered no stickiness or greasiness, felt appropriately wet, imparted a fresh feeling upon use, and underwent no change over time. The water repellency on the skin was favorable, and the retention was also good.

Example 18

Sunblock Cream

| (Components) | (%) |
| --- | --- |
| 1. Decamethylcyclopentasiloxane | 20.0 |
| 2. Liquid paraffin | 10.0 |
| 3. The organopolysiloxane of example 3 | 4.0 |
| 4. 4-t-butyl-4'-methoxydibenzoylmethane | 7.0 |
| 5. Distearyldimethylammonium chloride | 0.8 |
| 6. Vitamin E acetate | 0.1 |
| 7. Ethanol | 1.0 |
| 8. Aluminum magnesium silicate | 1.2 |
| 9. Preservative | appropriate amount |
| 10. Fragrance | appropriate amount |
| 11. Pure water | remainder |

(Production Method)

A: Components 1 to 6 and component 9 were mixed together under heat.

B: Components 7 to 8 and component 11 were mixed under heat to form a uniform dispersion.

C: Under constant stiffing, the dispersion obtained in B was added gradually to the mixture obtained in A and emulsified, the resulting emulsion was cooled, and component 10 was then added to complete preparation of a sunblock cream.

The sunblock cream obtained in this manner had a fine texture, exhibited good spreadability, and underwent no change over time. Further, because the cream exhibited no stickiness, no sand adhered to the skin, meaning the usability of the cream was excellent. Moreover, the cosmetic retention was also good, meaning a sustained ultraviolet blocking effect was obtained.

Example 19

Cream

| (Components) | (%) |
|---|---|
| 1. Decamethylcyclopentasiloxane | 10.0 |
| 2. Dimethylpolysiloxane (6 cs) | 5.0 |
| 3. Liquid paraffin | 5.0 |
| 4. The organopolysiloxane of example 2 | 5.0 |
| 5. Sodium citrate | 2.0 |
| 6. 1,3-butylene glycol | 5.0 |
| 7. Preservative | appropriate amount |
| 8. Fragrance | appropriate amount |
| 9. Pure water | remainder |

(Production Method)
A: Components 1 to 4 were mixed together under heat.
B: Components 5 to 7 were dissolved in component 9 under heat.
C: Under constant stirring, the solution obtained in B was added gradually to the mixture obtained in A and emulsified, the resulting emulsion was cooled, and component 8 was then added to complete preparation of a cream.

The cream obtained in this manner exhibited good spreadability, suffered no stickiness or greasiness, was moist and felt appropriately wet, imparted a fresh feeling upon use, and underwent no change over time. Further, the water resistance and water repellency on the skin were excellent, and the cosmetic retention was also good.

Example 20

Eye Shadow

| (Components) | (%) |
|---|---|
| 1. Decamethylcyclopentasiloxane | 15.0 |
| 2. Dimethylpolysiloxane (6 cs) | 10.0 |
| 3. The organopolysiloxane of example 1 | 2.0 |
| 4. PEG (10) lauryl ether | 0.5 |
| 5. Silicone-treated chromium oxide (note 1) | 6.2 |
| 6. Silicone-treated ultramarine blue (note 1) | 4.0 |
| 7. Silicone-treated titanium oxide-coated mica (note 1) | 6.0 |
| 8. Sodium chloride | 2.0 |
| 9. Propylene glycol | 8.0 |
| 10. Preservative | appropriate amount |
| 11. Fragrance | appropriate amount |
| 12. Pure water | remainder |

(note 1) Silicone treatment: 3% by mass of methylhydrogenpolysiloxane was added relative to the mass of the powder, and a heat treatment was then performed at 150° C.

(Production Method)
A: Components 1 to 4 were mixed, and components 5 to 7 were then added and dispersed uniformly.
B: Components 8 to 10 were dissolved in component 12.
C: Under constant stirring, the solution obtained in B was added gradually to the dispersion obtained in A and emulsified, the resulting emulsion was cooled, and component 11 was then added to complete preparation of an eye shadow.

The eye shadow obtained in this manner exhibited good spreadability, suffered no greasiness or powderiness, felt appropriately wet, imparted a fresh feeling upon use, exhibited favorable cosmetic retention with good levels of water resistance, water repellency and sweat resistance, was resistant to cosmetic breakdown, and also exhibited excellent stability, with no change upon temperature variation and no change over time.

Example 21

Eye Liner

| (Components) | (%) |
|---|---|
| 1. Decamethylcyclopentasiloxane | 22.0 |
| 2. Dimethylpolysiloxane (6 cs) | 5.0 |
| 3. Jojoba oil | 2.0 |
| 4. The organopolysiloxane of example 4 | 1.0 |
| 5. Silicone-treated black iron oxide (note 1) | 20.0 |
| 6. Ethanol | 5.0 |
| 7. Preservative | appropriate amount |
| 8. Pure water | remainder |

(note 1) Silicone-treated black iron oxide: 2% by mass of methylhydrogenpolysiloxane was added relative to the mass of the black iron oxide, and a heat treatment was then performed at 150° C.

(Production Method)
A: Components 1 to 4 were mixed together under heat, and component 5 was then added and dispersed uniformly.
B: Components 6 to 8 were dissolved under heat.
C: Under constant stirring, the solution obtained in B was added gradually to the dispersion obtained in A and emulsified, yielding an eye liner.

The eye liner obtained in this manner exhibited good spreadability, suffered no greasiness or powderiness, felt appropriately wet, imparted a fresh feeling upon use, and underwent no change over time. Further, the eye liner exhibited good cosmetic retention, with favorable levels of water repellency and sweat resistance, and was also resistant to cosmetic breakdown.

Example 22

Lip Cream

| (Components) | (%) |
|---|---|
| 1. Decamethylcyclopentasiloxane | 40.0 |
| 2. Isoparaffin (boiling point: 155° C.) | 10.0 |
| 3. Squalane | 10.0 |
| 4. Lanolin | 2.0 |
| 5. Trimethylsiloxy silicate | 3.0 |
| 6. Microcrystalline wax | 3.0 |
| 7. The organopolysiloxane of example 4 | 3.0 |
| 8. Lauroylglutamic acid dibutylamide | 5.0 |
| 9. Sodium lactate | 0.3 |
| 10. Sodium L-glutamate | 0.3 |
| 11. Sodium hyaluronate | 0.1 |
| 12. Sorbitol | 0.5 |

-continued

| (Components) | (%) |
|---|---|
| 13. Glycerol | 5.0 |
| 14. Red No. 202 | appropriate amount |
| 15. Menthol | appropriate amount |
| 16. Preservative | appropriate amount |
| 17. Fragrance | appropriate amount |
| 18. Pure water | remainder |

(Production Method)
A: Components 1 to 8 were mixed together under heat.
B: Components 9 to 16 were dissolved in component 18 under heat.
C: Under constant stiffing, the solution obtained in B was added gradually to the mixture obtained in A and emulsified, component 17 was added, and the resulting mixture was used to fill a capsule and complete preparation of a lip cream.

The solid water-in-oil lip cream obtained in this manner was readily spread, suffered no stickiness or greasiness, was moist and felt appropriately wet, imparted a fresh feeling upon use, and underwent no change over time. The cosmetic retention of the lip cream was also good.

Example 23

Liquid Emulsified Foundation

| (Components) | (%) |
|---|---|
| 1. Dimethylpolysiloxane (6 cs) | 5.0 |
| 2. Decamethylcyclopentasiloxane | 15.0 |
| 3. Squalane | 4.0 |
| 4. Neopentyl glycol dioctanoate | 3.0 |
| 5. Myristic acid isostearic acid diglyceride | 2.0 |
| 6. α-monoisostearyl glyceryl ether | 1.0 |
| 7. The organopolysiloxane of example 4 | 1.0 |
| 8. Aluminum distearate | 0.2 |
| 9. Hydrophobically treated titanium oxide (note 1) | 5.0 |
| 10. Hydrophobically treated sericite (note 1) | 2.0 |
| 11. Hydrophobically treated talc (note 1) | 3.0 |
| 12. Hydrophobically treated red iron oxide (note 1) | 0.4 |
| 13. Hydrophobically treated yellow iron oxide (note 1) | 0.7 |
| 14. Hydrophobically treated black iron oxide (note 1) | 0.1 |
| 15. Magnesium sulfate | 0.7 |
| 16. Glycerol | 3.0 |
| 17. Preservative | appropriate amount |
| 18. Fragrance | appropriate amount |
| 19. Pure water | remainder |

(note 1) Hydrophobically treated powders: treatment was performed using 2% by mass of stearic acid relative to the mass of the powder.

(Production Method)
A: Components 1 to 8 were mixed under heat, and components 9 to 14 were then added and dispersed uniformly.
B: Components 15 to 17 were dissolved in component 19 under heat.
C: Under constant stiffing, the solution obtained in B was added gradually to the mixture obtained in A and emulsified, the resulting emulsion was cooled, and component 18 was then added to complete preparation of a liquid emulsified foundation.

The liquid emulsified foundation obtained in this manner had a low viscosity and fine texture, was readily spread, suffered no stickiness or greasiness, was moist and felt appropriately wet, imparted a fresh feeling upon use, and underwent no change over time. The cosmetic retention on the skin was also good.

Example 24

Antiperspirant

| (Components) | (%) |
|---|---|
| 1. Octamethylcyclopentasiloxane | 30.0 |
| 2. The organopolysiloxane of example 3 | 1.0 |
| 3. Polyoxyethylene sorbitan monooleate (20 E.O.) | 0.5 |
| 4. Glycine salt of aluminum zirconium tetrachlorohydrate | 20.0 |
| 5. Pure water | remainder |

(Production Method)
A: Components 1 to 2 were mixed together.
B: Components 4 and 5 were dissolved, and component 3 was added.
C: Under constant stiffing, the solution obtained in B was added gradually to the mixture obtained in A and emulsified, yielding an antiperspirant.

The antiperspirant obtained in this manner exhibited good spreadability, suffered no stickiness or greasiness, resulted in minimal whitening, imparted a fresh feeling upon use, and underwent no change over time.

Example 25

Cleansing Cream

| (Components) | (%) |
|---|---|
| 1. Dimethylpolysiloxane (6 cs) | 5.0 |
| 2. Methylphenylpolysiloxane | 5.0 |
| 3. Liquid paraffin | 8.0 |
| 4. Jojoba oil | 2.0 |
| 5. The organopolysiloxane of example 1 | 2.5 |
| 6. The organopolysiloxane of example 2 | 0.5 |
| 7. Dextrin fatty acid ester | 0.8 |
| 8. Aluminum monostearate | 0.2 |
| 9. Aluminum chloride | 1.0 |
| 10. Glycerol | 10.0 |
| 11. Preservative | appropriate amount |
| 12. Fragrance | appropriate amount |
| 13. Pure water | remainder |

(Production Method)
A: Components 1 to 8 were mixed together under heat.
B: Components 9 to 11 were dissolved in component 13 under heat.
C: Under constant stiffing, the solution obtained in B was added gradually to the mixture obtained in A and emulsified, the resulting emulsion was cooled, and component 12 was then added to complete preparation of a cleansing cream.

The cleansing cream obtained in this manner had a fine texture, exhibited good spreadability, suffered no stickiness or greasiness, was moist and felt appropriately wet, imparted a fresh feeling upon use, exhibited a superior cleansing effect, and underwent no change over time.

Example 26

Cream

| (Components) | (%) |
| --- | --- |
| 1. Dimethylpolysiloxane (6 cs) | 7.0 |
| 2. Methylphenylpolysiloxane | 3.0 |
| 3. Squalane | 5.0 |
| 4. Neopentyl glycol dioctanoate | 3.0 |
| 5. The organopolysiloxane of example 2 | 3.0 |
| 6. Aluminum distearate | 0.4 |
| 7. Magnesium sulfate | 0.7 |
| 8. Glycerol | 10.0 |
| 9. Preservative | appropriate amount |
| 10. Fragrance | appropriate amount |
| 11. Pure water | remainder |

(Production Method)
A: Components 1 to 6 were mixed together uniformly under heat.
B: Components 7 to 9 were dissolved in component 11 under heat.
C: Under constant stiffing, the solution obtained in B was added gradually to the mixture obtained in A and emulsified, the resulting emulsion was cooled, and component 10 was then added to complete preparation of a cream.

The cream obtained in this manner had a fine texture, exhibited good spreadability, suffered no stickiness or greasiness, was moist and felt appropriately wet, imparted a fresh feeling upon use, and underwent no change over time. Further, the cosmetic retention on the skin was also extremely favorable.

Example 27

Cream

| (Components) | (%) |
| --- | --- |
| 1. Dimethylpolysiloxane (6 cs) | 6.0 |
| 2. Methylphenylpolysiloxane | 4.0 |
| 3. Squalane | 5.0 |
| 4. Neopentyl glycol dioctanoate | 3.0 |
| 5. The organopolysiloxane of example 3 | 3.0 |
| 6. Hydrophobically treated microparticulate titanium oxide (note 1) | 2.0 |
| 7. Magnesium sulfate | 0.7 |
| 8. Glycerol | 10.0 |
| 9. Preservative | appropriate amount |
| 10. Fragrance | appropriate amount |
| 11. Pure water | remainder |

(note 1) Hydrophobically treated microparticulate titanium oxide powder: Microparticulate titanium oxide with an average particle size of 0.05 μm was dispersed in water to generate a 10% dispersion, a 10% sodium silicate solution ($SiO_2/Na_2O$ molar ratio = 0.5) was added in an amount equivalent to providing 2% of $SiO_2$ relative to the titanium oxide, and following thorough stirring, a 10% aluminum sulfate solution was added gradually in an amount equivalent to providing 7.5% of $Al_2O_3$ relative to the titanium oxide, thereby depositing silicic acid hydrate and alumina hydrate on the surface of the titanium oxide. Following completion of the reaction, the mixture was filtered, washed and dried, and then pulverized using a jet mill. The resulting powder was transferred to a Henschel mixer, 2% of methylhydrogenpolysiloxane was added under vigorous stirring, and following thorough mixing, the mixture was subjected to a baking treatment at 120° C.

(Production Method)
A: Components 1 to 5 were mixed under heat, and component 6 was then added and mixed uniformly.
B: Components 7 to 9 were dissolved in component 11 under heat.
C: Under constant stiffing, the solution obtained in B was added gradually to the mixture obtained in A and emulsified, the resulting emulsion was cooled, and component 10 was then added to complete preparation of a cream.

The cream obtained in this manner had a fine texture, exhibited good spreadability, suffered no stickiness or greasiness, was moist and felt appropriately wet, imparted a fresh feeling upon use, and underwent no change over time. Further, the cosmetic retention on the skin was also extremely favorable.

Example 28

Transparent Gel Cosmetic Material

| (Components) | (%) |
| --- | --- |
| 1. Decamethylcyclopentasiloxane | 10.0 |
| 2. The organopolysiloxane of example 1 | 10.0 |
| 3. 1,3-butylene glycol | 10.0 |
| 4. Polyethylene glycol 400 | 9.0 |
| 5. 2-hydroxyoctanoic acid | 1.0 |
| 6. Sorbitol (70% aqueous solution) | 10.0 |
| 7. Citric acid | appropriate amount |
| 8. Sodium citrate | appropriate amount |
| 9. Preservative | appropriate amount |
| 10. Fragrance | appropriate amount |
| 11. Pure water | remainder |

(Production Method)
A: Components 3 to 11 were dissolved.
B: Components 1 and 2 were mixed and dispersed uniformly.
C: Under constant stirring, the solution obtained in A was added gradually to the mixture obtained in B and emulsified, yielding a transparent gel cosmetic material.

The transparent gel cosmetic material obtained in this manner exhibited good spreadability, suffered no stickiness or greasiness, was moist and felt appropriately wet, imparted a fresh feeling upon use, was readily compatible with the skin, and underwent no change over time.

Example 29

Sunblock Cosmetic Lotion

| (Components) | (%) |
| --- | --- |
| 1. Decamethylcyclopentasiloxane | 14.0 |
| 2. The organopolysiloxane of example 1 | 10.0 |
| 3. Squalane | 1.5 |
| 4. Octyl para-methoxycinnamate | 3.0 |
| 5. Hydrophobically treated ultrafine particulate titanium oxide (note 1) | 2.0 |
| 6. 1,3-butylene glycol | 10.0 |
| 7. Sodium chloride | 2.0 |
| 8. L-proline | 0.1 |
| 9. 2-hydroxyoctanoic acid | 1.0 |
| 10. 2-hydroxypropanoic acid | 5.0 |
| 11. Sodium hydroxide | appropriate amount |
| 12. Preservative | appropriate amount |
| 13. Fragrance | appropriate amount |
| 14. Pure water | remainder |

(note 1) Hydrophobically treated ultrafine particulate titanium oxide: TTO-V-4 (manufactured by Ishihara Sangyo Kaisha, Ltd.)

(Production Method)
A: Components 6 to 14 were dissolved.
B: Components 1 to 4 were mixed, and component 5 was then added and dispersed uniformly.
C: Under constant stiffing, B was added gradually to A and emulsified, yielding a sunblock cosmetic lotion.

The sunblock cosmetic lotion obtained in this manner exhibited good spreadability, suffered no stickiness or greasiness, was moist and felt appropriately wet, imparted a fresh feeling upon use, was readily compatible with the skin, and underwent no change over time. Moreover, the ultraviolet blocking effect was also excellent.

Example 30

Cream

| (Components) | (%) |
| --- | --- |
| 1. Decamethylcyclopentasiloxane | 20.0 |
| 2. Liquid paraffin | 5.0 |
| 3. The organopolysiloxane of example 4 | 1.0 |
| 4. Magnesium L-ascorbate phosphate | 3.0 |
| 5. Dipropylene glycol | 5.0 |
| 6. Glycerol | 5.0 |
| 7. Preservative | appropriate amount |
| 8. Fragrance | appropriate amount |
| 9. Pure water | remainder |

(Production Method)
A: Components 1 to 3 were mixed uniformly.
B: Components 5 to 7 were mixed uniformly under heat.
C: Component 4 was dissolved in component 9.
D: Under constant stirring, the mixture obtained in B was added gradually to the mixture obtained in A, the solution obtained in C was then added and emulsified, and component 8 was added to complete preparation of a cream.

The cream obtained in this manner had a fine texture, was readily spread, suffered no stickiness or greasiness, was moist and felt appropriately wet, imparted a fresh feeling upon use, exhibited good skin compatibility, and underwent no change over time. The cream also exhibited an excellent cosmetic whitening effect.

Example 31

Lotion

| (Components) | (%) |
| --- | --- |
| 1. Decamethylcyclopentasiloxane | 18.0 |
| 2. Dimethylpolysiloxane (6 cs) | 6.0 |
| 3. Squalane | 5.0 |
| 4. Neopentyl glycol dioctanoate | 3.0 |
| 5. α-monooleyl glyceryl ether | 1.0 |
| 6. The organopolysiloxane of example 4 | 2.0 |
| 7. Aluminum distearate | 0.2 |
| 8. Magnesium sulfate | 0.7 |
| 9. Glycerol | 5.0 |
| 10. Preservative | appropriate amount |
| 11. Fragrance | appropriate amount |
| 12. Pure water | remainder |

(Production Method)
A: Components 1 to 7 were mixed together under heat.
B: Components 8 to 10 were dissolved in component 12 under heat.
C: Under constant stiffing, the solution obtained in B was added gradually to the mixture obtained in A and emulsified, the resulting emulsion was cooled, and component 11 was then added to complete preparation of a lotion.

The lotion obtained in this manner had a low viscosity and a fine texture, exhibited good spreadability, suffered no stickiness or greasiness, was moist and felt appropriately wet, imparted a fresh feeling upon use, and underwent no change over time. Further, the lotion exhibited good cosmetic retention on the skin Example 32

Lotion

| (Components) | (%) |
| --- | --- |
| 1. Decamethylcyclopentasiloxane | 15.0 |
| 2. Dimethylpolysiloxane (6 cs) | 6.0 |
| 3. Squalane | 5.0 |
| 4. Neopentyl glycol dioctanoate | 3.0 |
| 5. α-monooleyl glyceryl ether | 1.0 |
| 6. Polyoxyalkylene/alkyl-comodified organopolysiloxane (note 1) | 1.5 |
| 7. The organopolysiloxane of example 4 | 1.0 |
| 8. Aluminum distearate | 0.2 |
| 9. Dextrin fatty acid ester | 1.0 |
| 10. Magnesium sulfate | 0.7 |
| 11. Glycerol | 5.0 |
| 12. Preservative | appropriate amount |
| 13. Fragrance | appropriate amount |
| 14. Pure water | remainder |

(note 1) Polyoxyalkylene/alkyl-comodified organopolysiloxane: KF6026 (manufactured by Shin-Etsu Chemical Co., Ltd.)

(Production Method)
A: Components 1 to 9 were mixed together under heat.
B: Components 10 to 12 were dissolved in component 14 under heat.
C: Under constant stirring, the solution obtained in B was added gradually to the mixture obtained in A and emulsified, the resulting emulsion was cooled, and component 13 was then added to complete preparation of a lotion.

The lotion obtained in this manner had a low viscosity and a fine texture, exhibited good spreadability, suffered no stickiness or greasiness, was moist and felt appropriately wet, imparted a fresh feeling upon use, and underwent no change over time. Further, the lotion exhibited good cosmetic retention on the skin Example 33

Sunblock Cream

| (Components) | (%) |
| --- | --- |
| 1. Decamethylcyclopentasiloxane | 18.0 |
| 2. Methylphenylpolysiloxane | 2.0 |
| 3. Liquid paraffin | 1.5 |
| 4. The organopolysiloxane of example 3 | 4.0 |
| 5. Octyl para-methoxycinnamate | 5.0 |
| 6. 1,3-butylene glycol | 4.0 |
| 7. Sodium chloride | 1.0 |
| 8. Preservative | appropriate amount |

| (Components) | (%) |
|---|---|
| 9. Fragrance | appropriate amount |
| 10. Pure water | remainder |

(Production Method)
A: Components 1 to 5 were mixed together under heat.
B: Components 6 to 8 were dissolved in component 10 under heat.
C: Under constant stiffing, the solution obtained in B was added gradually to the mixture obtained in A and emulsified, the resulting emulsion was cooled, and component 9 was then added to complete preparation of a sunblock cream.

The sunblock cream obtained in this manner had a fine texture, exhibited good spreadability, was moist and felt appropriately wet, suffered no greasiness or stickiness, and underwent no change over time. Further, the cream exhibited good cosmetic retention, with favorable levels of water resistance and sweat resistance, and provided a sustained ultraviolet blocking effect.

Example 34

Cream

| (Components) | (%) |
|---|---|
| 1. Decamethylcyclopentasiloxane | 20.0 |
| 2. Methylphenylpolysiloxane | 5.0 |
| 3. The organopolysiloxane of example 2 | 1.0 |
| 4. Dextrin fatty acid ester | 1.0 |
| 5. Glycerol | 5.0 |
| 6. Sodium chloride | 1.0 |
| 7. Preservative | appropriate amount |
| 8. Fragrance | appropriate amount |
| 9. Pure water | remainder |

(Production Method)
A: Components 1 to 4 were mixed together under heat.
B: Components 5 to 7 were dissolved in component 9 under heat.
C: Under constant stiffing, the solution obtained in B was added gradually to the mixture obtained in A and emulsified, the resulting emulsion was cooled, and component 8 was then added to complete preparation of a cream.

The cream obtained in this manner had a fine texture, exhibited good spreadability, was moist and felt appropriately wet, suffered no greasiness or stickiness, and underwent no change over time.

Example 35

Foundation

| (Components) | (%) |
|---|---|
| 1. Decamethylcyclopentasiloxane | 18.0 |
| 2. Methylphenylpolysiloxane | 5.0 |
| 3. Sorbitan monoisostearate | 0.5 |
| 4. Diglyceryl monoisostearate | 0.5 |
| 5. The organopolysiloxane of example 1 | 1.0 |
| 6. Octyl para-methoxycinnamate | 3.0 |
| 7. Titanium oxide | 10.0 |
| 8. Red iron oxide | 0.1 |
| 9. Yellow iron oxide | 0.3 |
| 10. Black iron oxide | 0.1 |
| 11. Talc | 2.5 |
| 12. Sorbitol | 2.0 |
| 13. Magnesium sulfate | 0.1 |
| 14. Ethanol | 10.0 |
| 15. Preservative | appropriate amount |
| 16. Fragrance | appropriate amount |
| 17. Pure water | remainder |

(Production Method)
A: Components 7 to 11 were mixed together uniformly.
B: Components 1 to 6 and component 15 were mixed together under heat, and the mixture obtained in A was then added and dispersed uniformly.
C: Components 12 to 13 were dissolved in component 17 under heat, the resulting solution was added to the dispersion obtained in B and emulsified, the resulting emulsion was cooled, and then components 14 and 16 were added to complete preparation of a foundation.

The foundation obtained in this manner suffered no stickiness, was readily spread, and imparted a fresh cooling sensation upon use. The emulsion state was favorable, and underwent no change over time.

Example 36

Liquid Foundation

| (Components) | (%) |
|---|---|
| 1. Decamethylcyclopentasiloxane | 15.0 |
| 2. Dimethylpolysiloxane (6 cs) | 5.0 |
| 3. Liquid paraffin | 3.0 |
| 4. The organopolysiloxane of example 1 | 1.5 |
| 5. Polyoxyalkylene-modified silicone (note 1) | 1.5 |
| 6. Palmitic acid | 0.5 |
| 7. Hydrophobic silica (note 2) | 5.0 |
| 8. Titanium oxide | 6.0 |
| 9. Red iron oxide | 0.3 |
| 10. Yellow iron oxide | 0.6 |
| 11. Black iron oxide | 0.1 |
| 12. Sericite | 8.0 |
| 13. Dipropylene glycol | 10.0 |
| 14. Magnesium sulfate | 2.0 |
| 15. Preservative | appropriate amount |
| 16. Antioxidant | appropriate amount |
| 17. Fragrance | appropriate amount |
| 18. Pure water | remainder |

(note 1) Polyoxyalkylene-modified silicone: KF6017 (manufactured by Shin-Etsu Chemical Co., Ltd.)
(note 2) Hydrophobic silica: Aerosil RY200 (manufactured by Nippon Aerosil Co., Ltd.)

(Production Method)
A: Components 8 to 12 were mixed together uniformly.
B: Components 1 to 7 and component 16 were mixed together under heat at 70° C., and the mixture obtained in A was then added and dispersed uniformly.
C: Components 13 to 18 were dissolved by heating at 70° C., the resulting solution was added to the dispersion obtained in B and emulsified, the resulting emulsion was cooled, and the component 17 was added, yielding a liquid foundation.

The liquid foundation obtained in this manner suffered no stickiness, was readily spread, and imparted a fresh cooling

Example 37

Sunblock Lotion

| (Components) | (%) |
|---|---|
| 1. Decamethylcyclopentasiloxane | 25.0 |
| 2. Diglyceryl monoisostearate | 1.5 |
| 3. Decaglyceryl pentaisostearate | 1.5 |
| 4. The organopolysiloxane of example 4 | 0.5 |
| 5. Olive oil | 1.0 |
| 6. Microparticulate titanium oxide | 7.0 |
| 7. Glycerol | 5.0 |
| 8. Sodium chloride | 1.5 |
| 9. Preservative | appropriate amount |
| 10. Fragrance | appropriate amount |
| 11. Pure water | remainder |

(Production Method)
A: Components 1 to 5 were mixed under heat, and component 6 was then added and dispersed uniformly.
B: Components 7 to 9 and component 11 were mixed together under heat.
C: Under constant stiffing, the mixture obtained in B was added gradually to the dispersion obtained in A and emulsified, the resulting emulsion was cooled, and component 10 was then added to complete preparation of a sunblock lotion.

The sunblock lotion obtained in this manner had a low viscosity and a fine texture, exhibited good spreadability, suffered no stickiness, imparted a moist feeling, and underwent no change over time. Further, the cosmetic retention was also good, and a sustained ultraviolet blocking effect was obtained.

Example 38

Sunblock Lotion

| (Components) | (%) |
|---|---|
| 1. Decamethylcyclopentasiloxane | 20.0 |
| 2. Methylphenylpolysiloxane | 3.0 |
| 3. Sorbitan monoisostearate | 1.0 |
| 4. The organopolysiloxane of example 2 | 0.5 |
| 5. Trimethylsiloxysilicic acid | 1.0 |
| 6. Octyl para-methoxycinnamate | 4.0 |
| 7. Microparticulate titanium oxide | 8.0 |
| 8. Sorbitol | 2.0 |
| 9. Sodium chloride | 2.0 |
| 10. Preservative | appropriate amount |
| 11. Fragrance | appropriate amount |
| 12. Pure water | remainder |

(Production Method)
A: Components 1 to 6 were mixed under heat, and component 7 was then added and dispersed uniformly.
B: Components 8 to 10 and component 12 were mixed together under heat.
C: Under constant stiffing, the mixture obtained in B was added gradually to the dispersion obtained in A and emulsified, the resulting emulsion was cooled, and component 11 was then added to complete preparation of a sunblock lotion.

The sunblock lotion obtained in this manner had a fine texture, exhibited good spreadability, suffered no stickiness, and underwent no change over time. Further, the cosmetic retention was also good, and a sustained ultraviolet blocking effect was obtained.

Example 39

Beauty Lotion

| (Components) | (%) |
|---|---|
| 1. Decamethylcyclopentasiloxane | 12.0 |
| 2. Glyceryl triisooctanoate | 10.0 |
| 3. Polyoxyalkylene/alkyl-comodified organopolysiloxane (note 1) | 2.0 |
| 4. The organopolysiloxane of example 2 | 0.2 |
| 5. Glycerol | 10.0 |
| 6. Magnesium ascorbate | 3.0 |
| 7. Sodium chloride | 2.0 |
| 8. Preservative | appropriate amount |
| 9. Fragrance | appropriate amount |
| 10. Pure water | remainder |

(note 1) Polyoxyalkylene/alkyl-comodified organopolysiloxane: KF6026 (manufactured by Shin-Etsu Chemical Co., Ltd.)

(Production Method)
A: Components 1 to 4 were mixed together under heat.
B: Components 5 to 8 were dissolved in component 10 under heat.
C: Under constant stiffing, the solution obtained in B was added gradually to the mixture obtained in A and emulsified, the resulting emulsion was cooled, and component 9 was then added to complete preparation of a beauty lotion.

The beauty lotion obtained in this manner had a fine texture, exhibited good spreadability, suffered no stickiness, imparted a moist feeling upon use, and underwent no change over time.

Example 40

Cream

| (Components) | (%) |
|---|---|
| 1. Decamethylcyclopentasiloxane | 18.0 |
| 2. Dimethylpolysiloxane (100 cs) | 2.0 |
| 3. Polypropylene glycol (3) myristyl ether | 0.5 |
| 4. The organopolysiloxane of example 1 | 2.5 |
| 5. Hydrophobically treated microparticulate titanium oxide (note 1) | 1.0 |
| 6. Glycerol | 3.0 |
| 7. 70% Sorbitol | 5.0 |
| 8. Citric acid | 25.0 |
| 9. Sodium chloride | 0.6 |
| 10. Preservative | appropriate amount |
| 11. Fragrance | appropriate amount |
| 12. 32% ammonia | 4.5 |
| 13. Pure water | remainder |

(note 1) Hydrophobically treated microparticulate titanium oxide: aluminum stearate-treated microparticulate titanium oxide (Production Method)
A: Components 1 to 4 and component 11 were mixed together, and component 5 was then added and mixed.
B: Components 6 to 10 were dissolved in components 12 and 13.

C: The solution obtained in B was added gradually to the mixture obtained in A and emulsified, thereby completing complete preparation of a cream.

Despite containing a large amount of citric acid, the cream obtained in this manner was readily spread, suffered no stickiness, felt moist but not sticky on the skin, and underwent no change over time.

Example 41

Rinse-Off Pack Cosmetic Material

| (Components) | (%) |
|---|---|
| 1. Dimethylpolysiloxane (6 cs) | 3.0 |
| 2. The organopolysiloxane of example 1 | 2.0 |
| 3. Kaolin | 30.0 |
| 4. Carboxyl vinyl ether | 0.4 |
| 5. 1,3-butylene glycol | 10.0 |
| 6. Glycerol | 20.0 |
| 7. Preservative | appropriate amount |
| 8. Fragrance | appropriate amount |
| 9. Pure water | remainder |

(Production Method)

A: Components 1 to 2 and component 8 were mixed together.

B: Components 4 to 7 and component 9 were mixed uniformly, and component 3 was then added and mixed.

C: The mixture obtained in A was added gradually to the mixture obtained in B and emulsified, yielding a paste-like rinse-off pack cosmetic material.

The rinse-off pack cosmetic material obtained in this manner was readily spread, and following removal by rinsing, left the skin feeling moist and silky. Further, the pack cosmetic material underwent no change over time.

Example 42

Wipeable Cleanser

| (Components) | (%) |
|---|---|
| 1. Squalane | 10.0 |
| 2. Liquid paraffin | 28.0 |
| 3. Low-density polyethylene | 2.0 |
| 4. The organopolysiloxane of example 1 | 2.0 |
| 5. Propylene glycol | 5.0 |
| 6. Antioxidant | appropriate amount |
| 7. Preservative | appropriate amount |
| 8. Fragrance | appropriate amount |
| 9. Pure water | remainder |

(Production Method)

A: Components 1 to 4 and components 6 to 8 were mixed together under heat.

B: Component 5 was dissolved in component 9 under heat, and under constant stiffing, the resulting solution was added gradually to the mixture obtained in A and emulsified, yielding a wipeable cleanser.

The wipeable cleanser obtained in this manner suffered no stickiness, was readily spread, and following removal by wiping, left the skin feeling moist. Further, the wipeable cleanser underwent no change over time.

Example 43

Aftershave Cream

| (Components) | (%) |
|---|---|
| 1. Decamethylcyclopentasiloxane | 35.0 |
| 2. The organopolysiloxane of example 2 | 5.0 |
| 3. Polyethylene glycol (molecular weight: 400) | 5.0 |
| 4. Sodium L-glutamate | 2.0 |
| 5. Allantoin | 0.1 |
| 6. Aloe extract | appropriate amount |
| 7. Preservative | appropriate amount |
| 8. Antioxidant | appropriate amount |
| 9. Fragrance | appropriate amount |
| 10. Pure water | remainder |

(Production Method)

A: Components 1 to 3 and components 9 and 10 were mixed together under heat.

B: Components 4 to 8 were mixed under heat.

C: The mixture obtained in B was added gradually to the mixture obtained in A and emulsified, yielding an aftershave cream.

The aftershave cream obtained in this manner exhibited excellent spreadability upon application, and suffered no stickiness. Further, following application, the cream did not drip or sag, and imparted a moist feeling to the skin. Further, the aftershave cream underwent no change over time.

Example 44

Deodorant

| (Components) | (%) |
|---|---|
| 1. Decamethylcyclopentasiloxane | 12.0 |
| 2. Dimethylpolysiloxane (6 cs) | 4.0 |
| 3. The organopolysiloxane of example 1 | 1.0 |
| 4. Propylene glycol | 31.0 |
| 5. Triclosan | 0.1 |
| 6. Glycerol | 15.0 |
| 7. Preservative | appropriate amount |
| 8. Fragrance | appropriate amount |
| 9. Pure water | remainder |

(Production Method)

A: Components 1 to 3 were mixed.

B: Component 5 was dissolved in component 4, and components 6 to 9 were added and mixed.

C: With the mixture obtained in A undergoing vigorous stirring, the mixture obtained in B was added and emulsified.

D: 65 parts of the mixture from C and 35 parts of a propellant (a mixture of n-butane, isobutane and propane) were combined in an aerosol can, completing preparation of a deodorant.

The deodorant obtained in this manner did not run even when sprayed on in large amounts, suffered no stickiness, and imparted a moist feeling and a sustained deodorant effect. Further, the deodorant underwent no change over time.

Example 45

Liquid Foundation

| (Components) | (%) |
|---|---|
| 1. Decamethylcyclopentasiloxane | 16.0 |
| 2. Dimethylpolysiloxane (6 cs) | 8.0 |
| 3. Octyl para-methoxycinnamate | 3.0 |
| 4. 12-hydroxystearic acid | 1.0 |
| 5. Fluorine-modified silicone (note 1) | 15.0 |
| 6. The organopolysiloxane of example 3 | 5.0 |
| 7. Spherical silicone resin powder (note 2) | 3.0 |
| 8. Fluorine compound-treated microparticulate titanium oxide (note 3) | 8.0 |
| 9. Fluorine compound-treated titanated mica (note 3) | 1.0 |
| 10. Fluorine compound-treated titanium oxide (note 3) | 5.0 |
| 11. Fluorine compound-treated red iron oxide (note 3) | 0.9 |
| 12. Fluorine compound-treated yellow iron oxide (note 3) | 2.0 |
| 13. Fluorine compound-treated black iron oxide (note 3) | 1.0 |
| 14. Ethanol | 15.0 |
| 15. Glycerol | 3.0 |
| 16. Magnesium sulfate | 1.0 |
| 17. Preservative | appropriate amount |
| 18. Fragrance | appropriate amount |
| 19. Pure water | remainder |

(note 1) Fluorine-modified silicone: FL-100 (manufactured by Shin-Etsu Chemical Co., Ltd.)
(note 2) Spherical silicone resin powder: KMP590 (manufactured by Shin-Etsu Chemical Co., Ltd.)
(note 3) Fluorine compound treatment: the material was coated with 5% of the diethanolamine salt of perfluoroalkylethylphosphoric acid (Production Method)

A: Components 7 to 13 were mixed together uniformly.
B: Components 1 to 6 were mixed together under heating at 70° C., and the mixture obtained in A was then added and dispersed uniformly.
C: Components 14 to 17 were dissolved in component 19 by heating at 40° C., the resulting solution was added gradually to the dispersion obtained in B and emulsified, the resulting emulsion was cooled, and component 18 was then added, yielding a liquid foundation.

The liquid foundation obtained in this manner suffered no stickiness, was readily spread, and imparted a fresh sensation upon use. Further, the liquid foundation underwent no change over time.

Example 46

Sunblock Lotion

| (Components) | (%) |
|---|---|
| 1. Pentaerythritol tetra-2-ethylhexanoate | 10.0 |
| 2. Cetyl 2-ethylhexanoate | 5.0 |
| 3. Squalane | 10.0 |
| 4. The organopolysiloxane of example 1 | 3.0 |
| 5. Octyl para-methoxycinnamate | 2.0 |
| 6. 2,4-dihydroxybenzophenone | 5.0 |
| 7. Organopolysiloxane elastomer spherical composite powder (note 1) | 1.5 |
| 8. Hydrophobic silica (note 2) | 0.5 |
| 9. Polyethylene glycol 6000 | 1.0 |
| 10. Propylene glycol | 8.0 |
| 11. Preservative | appropriate amount |
| 12. Fragrance | appropriate amount |
| 13. Pure water | remainder |

(note 1) Organopolysiloxane elastomer spherical composite powder: KSP-1 (manufactured by Shin-Etsu Chemical Co., Ltd.)
(note 2) Hydrophobic silica: Aerosil R972 (manufactured by Nippon Aerosil Co., Ltd.)

(Production Method)

A: Components 5 and 6 were dissolved in a portion of component 1.
B: The remainder of component 1 was mixed with components 2 to 4, the solution obtained in A was added, and components 7 and 8 were then added and dispersed uniformly.
C: Component 9 was dissolved in component 13, and a mixture of components 10 and 11 was added to the solution.
D: The mixture obtained in C was added gradually to the dispersion obtained in B and emulsified, the resulting emulsion was cooled, and component 12 was then added to complete preparation of a sunblock lotion.

The sunblock lotion obtained in this manner exhibited good spreadability, produced a dry touch with no stickiness, and underwent no change over time.

Example 47

Lotion

| (Components) | (%) |
|---|---|
| 1. Decamethylcyclopentasiloxane | 15.0 |
| 2. Methylphenylpolysiloxane | 5.0 |
| 3. Squalene | 5.0 |
| 4. Pentaerythritol tetra-2-ethylhexanoate | 5.0 |
| 5. The organopolysiloxane of example 1 | 3.0 |
| 6. Organopolysiloxane elastomer spherical powder (note 1) | 2.0 |
| 7. Hydrophobic silica (note 2) | 0.5 |
| 8. Magnesium ascorbate phosphate | 1.0 |
| 9. Sodium chloride | 1.0 |
| 10. Polyethylene glycol 11000 | 1.0 |
| 11. Propylene glycol | 8.0 |
| 12. Preservative | appropriate amount |
| 13. Fragrance | appropriate amount |
| 14. Pure water | remainder |

(note 1) Organopolysiloxane elastomer spherical powder: KMP594 (manufactured by Shin-Etsu Chemical Co., Ltd.)
(note 2) Hydrophobic silica: Aerosil R972 (manufactured by Nippon Aerosil Co., Ltd.)

(Production Method)

A: Components 1 to 5 were mixed uniformly, and components 6 and 7 were then added and dispersed uniformly.
B: Components 8 to 10 were dissolved in component 14, and a mixture of components 11 and 12 was added to the solution.
C: The mixture obtained in B was added gradually to the dispersion obtained in A and emulsified, the resulting emulsion was cooled, and component 13 was then added to complete preparation of a lotion.

The lotion obtained in this manner exhibited good spreadability, produced a dry touch with no stickiness, and underwent no change over time.

Example 48

Moisturizing Cream

| (Components) | (%) |
| --- | --- |
| 1. Decamethylcyclopentasiloxane | 10.0 |
| 2. Methylphenylpolysiloxane | 3.0 |
| 3. Liquid paraffin | 5.0 |
| 4. Pentaerythritol tetra-2-ethylhexanoate | 3.0 |
| 5. Cetyl 2-ethylhexanoate | 5.0 |
| 6. The organopolysiloxane of example 1 | 1.0 |
| 7. Organopolysiloxane elastomer spherical powder (note 1) | 2.5 |
| 8. Hydrophobic silica (note 2) | 2.0 |
| 9. Zinc stearate | 2.0 |
| 10. Vitamin E acetate | 3.0 |
| 11. Polyethylene glycol 400 | 1.0 |
| 12. Sodium lactate | 1.0 |
| 13. 1,3-butylene glycol | 5.0 |
| 14. Preservative | appropriate amount |
| 15. Fragrance | appropriate amount |
| 16. Pure water | remainder |

(note 1) Organopolysiloxane elastomer spherical powder: KMP594 (manufactured by Shin-Etsu Chemical Co., Ltd.)
(note 2) Hydrophobic silica: Aerosil R972 (manufactured by Nippon Aerosil Co., Ltd.)

(Production Method)
A: Components 1 to 6 and components 9 to 10 were mixed uniformly, and components 7 and 8 were then added and dispersed uniformly.
B: Components 11 to 14 were dissolved in component 16.
C: The solution obtained in B was added gradually to the mixture obtained in A and emulsified, the resulting emulsion was cooled, and component 15 was then added to complete preparation of a moisturizing cream.

The moisturizing cream obtained in this manner exhibited good spreadability, suffered no stickiness, and underwent no change over time.

Example 49

Hand Cream

| (Components) | (%) |
| --- | --- |
| 1. Decamethylcyclopentasiloxane | 30.0 |
| 2. Liquid paraffin | 10.0 |
| 3. Amino-modified silicone gum (note 1) | 15.0 |
| 4. The organopolysiloxane of example 4 | 4.0 |
| 5. Distearyldimethylammonium chloride | 0.8 |
| 6. Vitamin E acetate | 0.1 |
| 7. Polyethylene glycol 4000 | 1.0 |
| 8. Glycerol | 10.0 |
| 9. Aluminum magnesium silicate | 1.2 |
| 10. Preservative | appropriate amount |
| 11. Fragrance | appropriate amount |
| 12. Pure water | remainder |

(note 1) Amine equivalent weight: 70,000 g/mol (Production Method)
A: Components 1 and 3 were dissolved under heat, and components 2, 4 to 6, and 10 were then added under heat.
B: Components 7 to 9 and component 12 were mixed under heat.
C: The mixture obtained in B was added gradually to the mixture obtained in A and emulsified, the resulting emulsion was cooled, and component 11 was then added to complete preparation of a hand cream.

The hand cream obtained in this manner exhibited good spreadability, suffered no stickiness, imparted a fresh feeling, and underwent no change over time. The hand cream protected the skin effectively from wet work.

Example 50

Eye Liner

| (Components) | (%) |
| --- | --- |
| 1. Decamethylcyclopentasiloxane | 22.0 |
| 2. Dimethylpolysiloxane (6 cs) | 5.0 |
| 3. Silicone-treated black iron oxide | 20.0 |
| 4. Vitamin E acetate | 0.2 |
| 5. Jojoba oil | 2.0 |
| 6. Bentonite | 3.0 |
| 7. The organopolysiloxane of example 3 | 2.0 |
| 8. Ethanol | 10.0 |
| 9. 1,3-butylene glycol | 10.0 |
| 10. Preservative | appropriate amount |
| 11. Fragrance | appropriate amount |
| 12. Pure water | remainder |

(Production Method)
A: Components 1 and 2, and components 4 to 7 were mixed, and component 3 was then added and dispersed uniformly.
B: Components 8 to 10 and component 12 were mixed.
C: The mixture obtained in B was added gradually to the dispersion obtained in A and emulsified, the resulting emulsion was cooled, and component 11 was then added to complete preparation of an eye liner.

The eye liner obtained in this manner was readily spread and easy to draw, and underwent no change over time. Further, the eye liner exhibited excellent water resistance and sweat resistance on the skin, and also displayed excellent cosmetic retention.

Example 51

Cream

| (Components) | (%) |
| --- | --- |
| 1. Decamethylcyclopentasiloxane | 16.0 |
| 2. Dimethylpolysiloxane (6 cs) | 4.0 |
| 3. The organopolysiloxane of example 3 | 5.0 |
| 4. POE (5) octyl dodecyl ether | 1.0 |
| 5. Polyoxyethylene sorbitan monostearate (20 E.O.) | 0.5 |
| 6. Silicic anhydride-treated zinc oxide (note 1) | 2.0 |
| 7. Silicone-treated microparticulate titanium oxide | 10.0 |
| 8. Liquid paraffin | 2.0 |
| 9. Macadamia nut oil | 1.0 |
| 10. Scutellaria baicalensis root extract (note 2) | 1.0 |
| 11. Gentian extract (note 3) | 0.5 |
| 12. Ethanol | 5.0 |
| 13. 1,3-butylene glycol | 2.0 |

-continued

| (Components) | (%) |
|---|---|
| 14. Preservative | appropriate amount |
| 15. Fragrance | appropriate amount |
| 16. Pure water | remainder |

(note 1) Silicic anhydride-treated zinc oxide: Silica particles with a particle size of 0.01 to 10 μm containing 50% of encapsulated zinc oxide, product name: Sunsphere SZ-5 (manufactured by Asahi Glass Co., Ltd.)
(note 2) Baikal Skullcap extract: Extracted using 50% 1,3-butylene glycol water
(note 3) Gentian extract: Extracted using 20% ethanol water (Production Method)
A: Components 6 to 9 were mixed uniformly.
B: Components 1 to 5 were mixed together, and the mixture obtained in A was then added.
C: Components 10 to 14 and component 16 were mixed, and the mixture obtained in B was then added and emulsified.
D: The emulsion obtained in C was cooled, and component 15 was then added to complete preparation of a cream.

The cream obtained in this manner suffered no stickiness, was readily spread, exhibited a superior feeling of adhesion, yielded a lustrous finish, and underwent no change over time.

Example 52

Foundation

| (Components) | (%) |
|---|---|
| 1. Decamethylcyclopentasiloxane | 27.0 |
| 2. Methylphenylpolysiloxane | 3.0 |
| 3. Glyceryl triisooctanoate | 10.0 |
| 4. The organopolysiloxane of example 1 | 1.0 |
| 5. Polyglyceryl monoisostearate | 3.0 |
| 6. Hydrophobically treated mixed powder (note 1) | 18.0 |
| 7. Red iron oxide | 1.2 |
| 8. Yellow iron oxide | 2.6 |
| 9. Black iron oxide | 0.2 |
| 10. 1,3-butylene glycol | 7.0 |
| 11. Sodium chloride | 0.5 |
| 12. Preservative | appropriate amount |
| 13. Fragrance | appropriate amount |
| 14. Pure water | remainder |

(note 1) Hydrophobically treated mixed powder:
a. Microparticulate titanium oxide  8.0
b. Microparticulate zinc oxide  4.0
c. Talc  3.0
d. Mica  3.0

(Production Method)
A: Components a to d were mixed, 1% by mass of methylhydrogenpolysiloxane was added relative to the total mass of the mixed powder, and the resulting mixture was subjected to a heat treatment at 150° C.
B: Components 1 to 5 were mixed and dissolved under heat, and then components 6 to 9 were dispersed uniformly within the solution.
C: Components 10 to 12 and component 14 were mixed, and the dispersion obtained in B was then added and emulsified.
D: The emulsion from C was cooled, and component 13 was then added to complete preparation of a foundation.

The foundation obtained in this manner suffered no stickiness, exhibited good spreadability, imparted a favorable feeling of adhesion, and underwent no change over time. The foundation yielded a lustrous finish, and also exhibited very good cosmetic retention.

Example 53

Makeup Remover

| (Components) | (%) |
|---|---|
| 1. The organopolysiloxane of example 2 | 20.0 |
| 2. Polyoxyethylene (20) sorbitan monostearate | 10.0 |
| 3. Sorbitol | 10.0 |
| 4. Carrageenan | 0.5 |
| 5. Preservative | appropriate amount |
| 6. Fragrance | appropriate amount |
| 7. Pure water | remainder |

(Production Method)
A: Components 1 to 5 were dissolved in component 7.
B: Component 6 was added to the solution obtained in A, yielding a makeup remover.

When a foundation was removed using the makeup remover obtained in this manner, the degree of removal of the foundation and sebum soiling was excellent. The makeup remover was also readily spread upon use, produced no stickiness following use, and underwent no change over time.

Example 54

Hair Makeup Remover

| (Components) | (%) |
|---|---|
| 1. The organopolysiloxane of example 4 | 10.0 |
| 2. Diethylene glycol monoethyl ether | 5.0 |
| 3. Glycerol | 30.0 |
| 4. Carrageenan | 0.5 |
| 5. Preservative | appropriate amount |
| 6. Fragrance | appropriate amount |
| 7. Pure water | remainder |

(Production Method)
A: Components 1 to 5 were dissolved in component 7.
B: Component 6 was added to the solution obtained in A, yielding a hair makeup remover.

When hair was washed using the hair makeup remover obtained in this manner, the degree of removal of hair makeup and sebum soiling was excellent. The hair makeup remover was also readily spread upon use, yielded a dry feeling with no stickiness following use, and underwent no change over time.

Example 55

Sunblock Cream

| (Components) | (%) |
|---|---|
| 1. Decamethylcyclopentasiloxane | 17.5 |
| 2. KP545 (note 1) | 12.0 |

-continued

| (Components) | (%) |
|---|---|
| 3. Glyceryl triisooctanoate | 5.0 |
| 4. Octyl para-methoxycinnamate | 6.0 |
| 5. KSG21 (note 2) | 5.0 |
| 6. The organopolysiloxane of example 3 | 1.0 |
| 7. Lipophilically treated zinc oxide | 20.0 |
| 8. Sodium chloride | 0.5 |
| 9. 1,3-butylene glycol | 2.0 |
| 10. Preservative | appropriate amount |
| 11. Fragrance | appropriate amount |
| 12. Pure water | remainder |

(note 1) KP545, an acrylic silicone (manufactured by Shin-Etsu Chemical Co., Ltd.)
(note 2) KSG21, a silicone gel (manufactured by Shin-Etsu Chemical Co., Ltd.)

(Production Method)

A: Component 2 was added to a portion of component 1 and mixed uniformly, and component 7 was then added and dispersed using a beads mill B: The remainder of component 1 and components 3 to 6 were mixed together uniformly.

C: Components 8 to 10 were dissolved in component 12.

D: The solution obtained in C was added to the mixture obtained in B and emulsified, and the mixture from A and component 11 were then added to complete preparation of a sunblock cream.

The sunblock cream obtained in this manner exhibited no stickiness, and exhibited good spreadability and adhesion. The sunblock cream also underwent no change over time, and produced a sustained ultraviolet blocking effect on the skin Example 56

O/W Hand Cream

| (Components) | (%) |
|---|---|
| 1. KP545 (note 1) | 10.0 |
| 2. KSG16 (note 2) | 2.0 |
| 3. Isoparaffin | 5.0 |
| 4. Vaseline | 5.0 |
| 5. Glyceryl triisooctanoate | 3.0 |
| 6. The organopolysiloxane of example 4 | 0.5 |
| 7. Polyoxyethylene sorbitan monooleate | 1.0 |
| 8. Sepigel 305(note 3) | 2.0 |
| 9. 1,3-butylene glycol | 5.0 |
| 10. Glycerol | 5.0 |
| 11. Preservative | appropriate amount |
| 12. Fragrance | appropriate amount |
| 13. Pure water | remainder |

(note 1) KP545, an acrylic silicone (manufactured by Shin-Etsu Chemical Co., Ltd.)
(note 2) KSG16, a silicone gel (manufactured by Shin-Etsu Chemical Co., Ltd.)
(note 3) Sepigel 305 (manufactured by Seppic Corporation)

(Production Method)

A: Components 1 to 7 were mixed uniformly.

B: Components 8 to 11 and component 13 were mixed uniformly.

C: The solution obtained in B was added to the mixture obtained in A and emulsified, and component 12 was then added to complete preparation of an O/W hand cream.

The hand cream obtained in this manner exhibited good spreadability, imparted a superior feeling of adhesion, and protected the skin effectively from wet work. The cream also underwent no change over time.

Example 57

O/W Hand Cream

| (Components) | (%) |
|---|---|
| 1. KP545 (note 1) | 10.0 |
| 2. KP561 (note 2) | 8.0 |
| 3. Cetanol | 1.0 |
| 4. Glyceryl triisooctanoate | 5.0 |
| 5. Stearic acid | 3.0 |
| 6. Glyceryl monostearate | 1.5 |
| 7. The organopolysiloxane of example 1 | 0.7 |
| 8. Sorbitan sesquioleate | 0.5 |
| 9. Polyoxyethylene sorbitan monooleate | 1.0 |
| 10. Sodium hydroxide (1% aqueous solution) | 10.0 |
| 11. 1,3-butylene glycol | 5.0 |
| 12. Preservative | appropriate amount |
| 13. Fragrance | appropriate amount |
| 14. Pure water | remainder |

(note 1) KP545, an acrylic silicone (manufactured by Shin-Etsu Chemical Co., Ltd.)
(note 2) KP561, a stearyl-modified acrylic silicone (manufactured by Shin-Etsu Chemical Co., Ltd.)

(Production Method)

A: Components 1 to 9 were mixed and dissolved under heat.

B: Components 10 to 12 and component 14 were mixed under heat.

C: The mixture obtained in B was added to the solution obtained in A and emulsified, the resulting emulsion was cooled, and component 13 was then added to complete preparation of an O/W hand cream.

The hand cream obtained in this manner suffered no stickiness, exhibited good spreadability, imparted a superior feeling of adhesion, and protected the skin effectively from wet work. The cream also underwent no change over time.

Example 58

A reaction container was charged with 234 parts by mass of an organohydrogenpolysiloxane represented by formula (10) shown below,

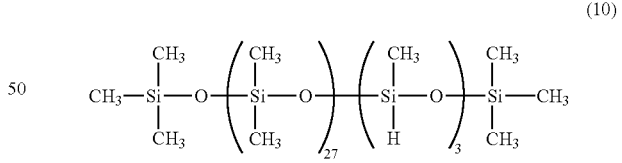

(10)

44.1 parts by mass of allylsuccinic anhydride represented by formula (11) shown below,

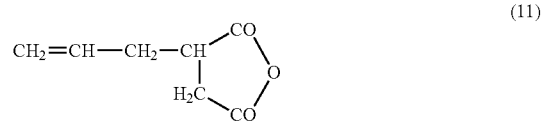

(11)

and 100 parts by mass of toluene, and following the addition of 0.1 parts of a 0.5% by mass toluene solution of chloroplatinic acid, the resulting mixture was reacted for 2 hours under reflux. The toluene was then removed by distillation by heating the reaction product under reduced pressure, yielding an acid anhydride group-containing organopolysiloxane represented by formula (12) shown below.

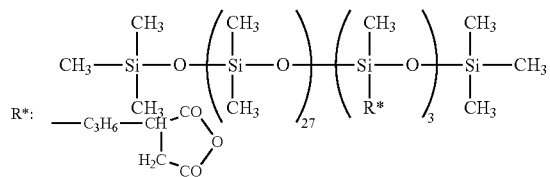
(12)

To 250 parts by mass of this acid anhydride group-containing organopolysiloxane were added 100 parts by mass of tetrahydrofuran and 50.3 parts by mass of laurylamine, and the resulting mixture was reacted for 2 hours under reflux. The solvent was then removed from the reaction product by distillation under reduced pressure, yielding a carboxyl group-containing organopolysiloxane represented by formula (24) shown below.

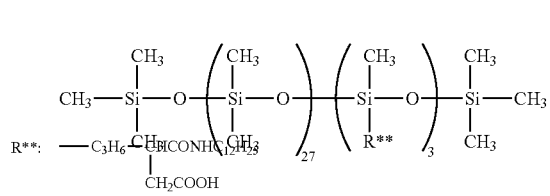
(24)

Example 59

A reaction container was charged with 241 parts by mass of an organohydrogenpolysiloxane represented by formula (14) shown below,

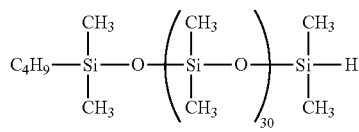
(14)

14.7 parts by mass of allylsuccinic anhydride represented by formula (11) above, and 100 parts by mass of toluene, and following the addition of 0.1 parts of a 0.5% by mass toluene solution of chloroplatinic acid, the resulting mixture was reacted for 2 hours under reflux. The solvent was then removed by distillation by heating the reaction product under reduced pressure, yielding an acid anhydride group-containing organopolysiloxane represented by formula (15) shown below.

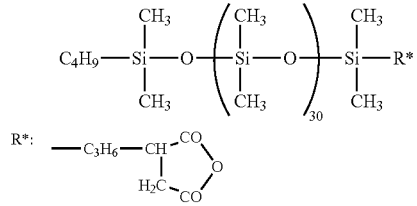
(15)

To 255 parts by mass of this acid anhydride group-containing organopolysiloxane were added 100 parts by mass of tetrahydrofuran and 26.9 parts by mass of stearylamine, and the resulting mixture was reacted for 2 hours under reflux. The solvent was then removed from the reaction product by distillation under reduced pressure, yielding a carboxyl group-containing organopolysiloxane represented by formula (25) shown below.

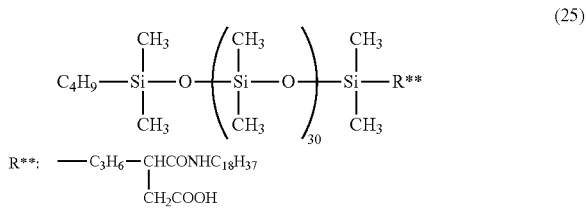
(25)

Example 60

A reaction container was charged with 340 parts by mass of an organohydrogenpolysiloxane represented by formula (26) shown below,

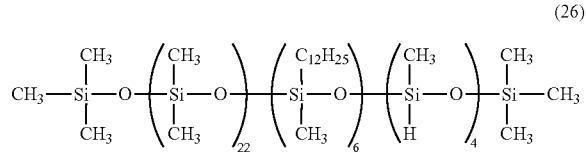
(26)

58.8 parts by mass of allylsuccinic anhydride represented by formula (11) above, and 100 parts by mass of toluene, and following the addition of 0.1 parts of a 0.5% by mass toluene solution of chloroplatinic acid, the resulting mixture was reacted for 2 hours under reflux. The solvent was then removed by distillation by heating the reaction product under reduced pressure, yielding an acid anhydride group-containing organopolysiloxane represented by formula (27) shown below.

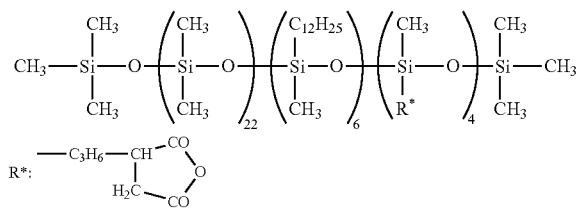
(27)

To 250 parts by mass of this acid anhydride group-containing organopolysiloxane were added 100 parts by mass of tetrahydrofuran and 67.4 parts by mass of N-hexyllaurylamine, and the resulting mixture was reacted for 2 hours under reflux. The solvent was then removed from the reaction product by distillation under reduced pressure, yielding a carboxyl group-containing organopolysiloxane represented by formula (28) shown below.

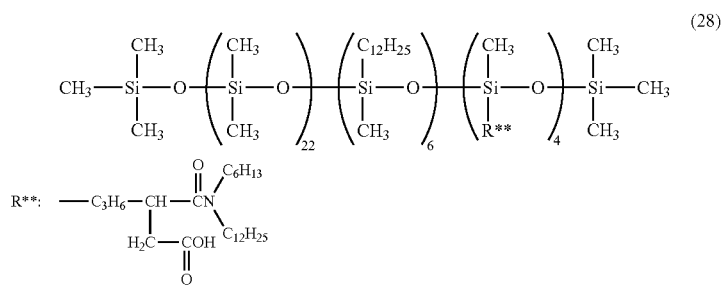
(28)

Example 61

A reaction container was charged with 240 parts by mass of an organohydrogenpolysiloxane represented by formula (20) shown below,

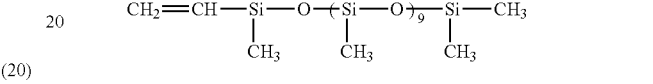
(20)

28.0 parts by mass of allylsuccinic anhydride represented by formula (11) above, 168 parts by mass of an organopolysiloxane having a vinyl group at one terminal, represented by formula (21) shown below,

(21)

and 100 parts by mass of toluene, and following the addition of 0.1 parts of a 0.5% by mass toluene solution of chloroplatinic acid, the resulting mixture was reacted for 2 hours under reflux. The solvent was then removed by distillation by heating the reaction product under reduced pressure, yielding an acid anhydride group-containing organopolysiloxane represented by formula (22) shown below.

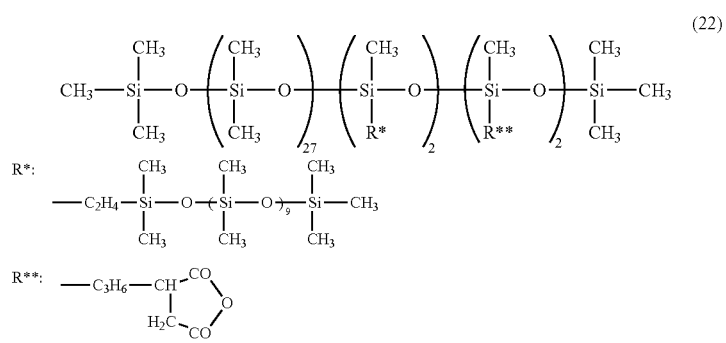
(22)

To 250 parts by mass of this acid anhydride group-containing organopolysiloxane were added 100 parts by mass of tetrahydrofuran and 10.4 parts by mass of laurylamine, and the resulting mixture was reacted for 5 hours under reflux. The solvent was then removed from the reaction product by distillation under reduced pressure, yielding a carboxyl group-containing organopolysiloxane represented by formula (29) shown below.

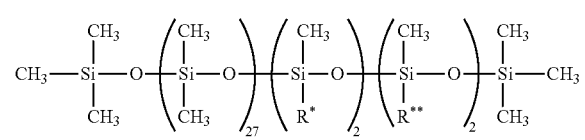
(29)

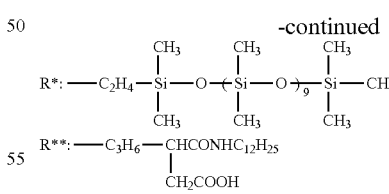

Examples 62 to 65, Comparative Examples 5 to 9

Emulsified cosmetic materials having the formulations shown in Table 5 below (blend amounts are shown as % by mass) were prepared using the method described below.
(Preparation Method)
Components 1 to 13 were mixed together at 1,500 rpm using a disper mixer, and component 14 was then added gradually and emulsified. A 100 g sample of the thus obtained emulsified cosmetic material was placed inside a sealed container and left to stand at room temperature for one week, and the emulsion state was then inspected and evaluated against the following criteria.

(Evaluation criteria) O: no separation, Δ: slight separation, x: separation into two phases As shown in Table 5, the cosmetic materials of comparative examples 5, 6, 8 and 9, which contained an alkyl-modified silicone that lacked amide bonds, suffered from poor stability of the emulsion system. The cosmetic material of comparative example 9 separated into two phases particularly quickly. Further, comparative example 7, in which the number of

TABLE 5

| | | Example | | | | Comparative example | | | | |
|---|---|---|---|---|---|---|---|---|---|---|
| | Component | 62 | 63 | 64 | 65 | 5 | 6 | 7 | 8 | 9 |
| 1 | The organopolysiloxane of example 58 | 6 | — | — | — | — | — | — | — | — |
| 2 | The organopolysiloxane of example 59 | — | 6 | — | — | — | — | — | — | — |
| 3 | The organopolysiloxane of example 60 | — | — | 6 | — | — | — | — | — | — |
| 4 | The organopolysiloxane of example 61 | — | — | — | 6 | — | — | — | — | — |
| 5 | Alkyl-modified polysiloxane (note 1) | — | — | — | — | 6 | — | — | — | — |
| 6 | Alkyl-modified polysiloxane (note 2) | — | — | — | — | — | 6 | — | — | — |
| 7 | Polysiloxane (note 3) | — | — | — | — | — | — | 6 | — | — |
| 8 | Polysiloxane (note 4) | — | — | — | — | — | — | — | 6 | — |
| 9 | Polyether-modified polysiloxane (note 5) | 2 | — | 2 | — | — | — | 2 | 2 | — |
| 10 | Polyether-modified polysiloxane (note 6) | — | 2 | — | 2 | 2 | 2 | — | — | 2 |
| 11 | Dimethylpolysiloxane (6 mm²/s) | 6 | 6 | 6 | 6 | 6 | 6 | 6 | 6 | 12 |
| 12 | Glyceryl tri-2-ethylhexanoate | 6 | 6 | 6 | 6 | 6 | 6 | 6 | 6 | 6 |
| 13 | Octyl para-methoxycinnamate | 6 | 6 | 6 | 6 | 6 | 6 | 6 | 6 | 6 |
| 14 | Water | 74 | 74 | 74 | 74 | 74 | 74 | 74 | 74 | 74 |
| | Stability | O | O | O | O | Δ | Δ | Δ | Δ | x |

(note 1) The alkyl-modified polysiloxane represented by the formula below.

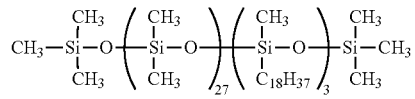

(note 2) The alkyl-modified polysiloxane represented by the formula below.

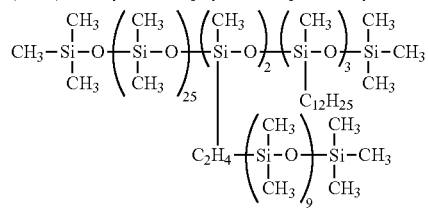

(note 3) The polysiloxane represented by the formula below.

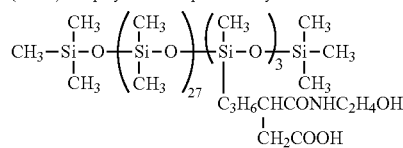

(note 4) The polysiloxane represented by the formula below.

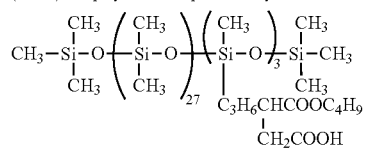

(note 5) The polyether-modified polysiloxane represented by the formula below.

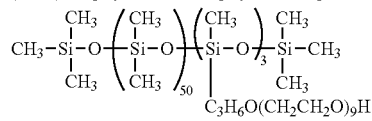

(note 6) The polyether-modified polysiloxane represented by the formula below.

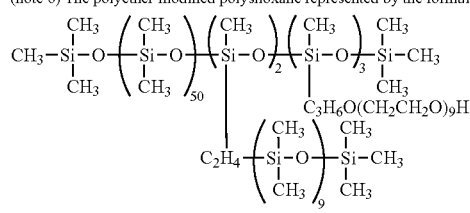

carbon atoms of the group bonded to the nitrogen atom was less than the range specified in the present invention, also exhibited unsatisfactory emulsion stability. In contrast, the cosmetic materials of examples 62 to 65 all retained the initial emulsion state even after standing for one week.

Examples 66 to 69, Comparative Examples 10 to 13

Using the organopolysiloxanes obtained in examples 58 to 61, W/O cream foundations having the formulations (units: parts by mass) shown in Table 6 below were prepared and then evaluated by 50 specialist female panelists.

The thus obtained foundations were subjected to actual usage tests by 50 specialist female panelists, and the skin adhesion, spreadability, uniformity of the cosmetic film and cosmetic retention were each evaluated against the criteria listed below.

[Evaluation Criteria]
  5 points: Very good
  4 points: Good
  3 points: Fair
  2 points: Slightly poor
  1 point: Poor

TABLE 6

|  | Component | Example 66 | Example 67 | Example 68 | Example 69 | Comparative example 10 | Comparative example 11 | Comparative example 12 | Comparative example 13 |
|---|---|---|---|---|---|---|---|---|---|
| 1 | The organopolysiloxane of example 58 | 5 | — | — | — | — | — | — | — |
| 2 | The organopolysiloxane of example 59 | — | 5 | — | — | — | — | — | — |
| 3 | The organopolysiloxane of example 60 | — | — | 5 | — | — | — | — | — |
| 4 | The organopolysiloxane of example 61 | — | — | — | 5 | — | — | — | — |
| 5 | Alkyl-modified polysiloxane(note 1) | — | — | — | — | 5 | — | — | — |
| 6 | Alkyl-modified polysiloxane(note 2) | — | — | — | — | — | 5 | — | — |
| 7 | Polysiloxane(note 3) | — | — | — | — | — | — | 5 | — |
| 8 | Polysiloxane(note 4) | — | — | — | — | — | — | — | 5 |
| 9 | Octyl para-methoxycinnamate | 5 | 5 | 5 | 5 | 5 | 5 | 5 | 5 |
| 10 | Polyether-modified polysiloxane(note 5) | 1 | 1 | 1 | 1 | 1 | 1 | 1 | 1 |
| 11 | Dimethylpolysiloxane (6 mm$^2$/s) | 3 | 3 | 3 | 3 | 3 | 3 | 3 | 3 |
| 12 | Decamethylcyclopentasiloxane | 10 | 10 | 10 | 10 | 10 | 10 | 10 | 10 |
| 13 | Isotridecyl isononanoate | 5 | 5 | 5 | 5 | 5 | 5 | 5 | 5 |
| 14 | Neopentyl glycol dioctanoate | 2 | 2 | 2 | 2 | 2 | 2 | 2 | 2 |
| 15 | Hybrid silicone complex powder(note 6) | 1.5 | 1.5 | 1.5 | 1.5 | 1.5 | 1.5 | 1.5 | 1.5 |
| 16 | Cross-linked glycerol-modified silicone composition(note 7) | 2 | 2 | 2 | 2 | 2 | 2 | 2 | 2 |
| 17 | Silicone-treated pigment(note 8) | 5 | 5 | 5 | 5 | 5 | 5 | 5 | 5 |
| 18 | Propylene glycol | 5 | 5 | 5 | 5 | 5 | 5 | 5 | 5 |
| 19 | Sodium chloride | 0.5 | 0.5 | 0.5 | 0.5 | 0.5 | 0.5 | 0.5 | 0.5 |
| 20 | Sodium citrate | 0.2 | 0.2 | 0.2 | 0.2 | 0.2 | 0.2 | 0.2 | 0.2 |
| 21 | Preservative | appropriate amount | appropriate amount | appropriate amount | appropriate amount | appropriate amount | appropriate amount | appropriate amount | appropriate amount |
| 22 | Fragrance | appropriate amount | appropriate amount | appropriate amount | appropriate amount | appropriate amount | appropriate amount | appropriate amount | appropriate amount |
| 23 | Water | remainder | remainder | remainder | remainder | remainder | remainder | remainder | remainder |

(note 1) to (note 5) are as described above for (note 1) to (note 5) of examples 62 to 65 and comparative examples 5 to 9.
(note 6) Hybrid silicone complex powder: KSP-100, manufactured by Shin-Etsu Chemical Co., Ltd.
(note 7) Cross-linked glycerol-modified silicone composition: KSG-710, manufactured by Shin-Etsu Chemical Co., Ltd.
(note 8) Silicone-treated pigment: 2% by mass of methylhydrogenpolysiloxane was added relative to the mass of the pigment, and a heat treatment was then performed at 150° C.

(Production Method)
A: Components 1 to 11, a portion of component 12, and components 13 to 15 were mixed together.
B: Components 16 and 17, and the remainder of component 12 were mixed.
C: Components 18 to 21 were dissolved in component 23.
D: The solution obtained in C was added to the mixture obtained in A and emulsified.
E: Component 22, the mixture obtained in B and the emulsion obtained in D were mixed uniformly, yielding a foundation.

For each evaluated property, the average number of points across all the panelists was recorded. In Table 7, the meanings of the grades awarded are as listed below.

Average number of points:
  4.5 points or higher: A
  At least 3.5 points but less than 4.5 points: B
  At least 2.5 points but less than 3.5 points: C
  At least 1.5 points but less than 2.5 points: D
  Less than 1.5 points: E

TABLE 7

|  | Example 66 | Example 67 | Example 68 | Example 69 | Comparative example 10 | Comparative example 11 | Comparative example 12 | Comparative example 13 |
|---|---|---|---|---|---|---|---|---|
| Skin adhesion | B | A | B | B | B | C | B | B |
| Spreadability | A | B | A | A | B | C | C | C |
| Cosmetic film uniformity | A | A | A | A | B | B | B | B |

| | Example 66 | Example 67 | Example 68 | Example 69 | Comparative example 10 | Comparative example 11 | Comparative example 12 | Comparative example 13 |
|---|---|---|---|---|---|---|---|---|
| Cosmetic retention | A | A | A | A | C | C | C | C |

As illustrated in Table 7, comparative examples 10, 11 and 13, which used an alkyl-modified silicone that lacked amide bonds, exhibited relatively poor dispersibility of the pigment, and displayed inferior spreadability and cosmetic film uniformity. Further, when these foundations were left to stand for one week at room temperature, the pigment precipitated out of the foundation. Moreover, the foundations of comparative examples 10, 12 and 13 displayed good adhesion at the time of application, but the spreadability and cosmetic retention were poor. In contrast, the foundations of examples 66 to 69 displayed a fine texture for the dispersion system, exhibited good spreadability, formed a uniform cosmetic film, and provided good cosmetic retention.

In the following examples, stability over time was evaluated by placing the cosmetic material in a sealed container, leaving the container to stand for one month at 50° C., and then checking that the material had undergone no change in external appearance.

Example 70

W/O Cream

| (Components) | (%) |
|---|---|
| 1. The organopolysiloxane of example 58 | 6.0 |
| 2. Liquid paraffin | 3.5 |
| 3. Macadamia nut oil | 4.0 |
| 4. Dimethylpolysiloxane (viscosity: 6 mm²/s at 25° C.) | 5.0 |
| 5. Octyl para-methoxycinnamate | 5.0 |
| 6. Polyglycerol-modified silicone (note 1) | 1.5 |
| 7. Propylene glycol | 8.0 |
| 8. Glycerol | 3.0 |
| 9. Preservative | appropriate amount |
| 10. Fragrance | appropriate amount |
| 11. Pure water | 64.0 |

(note 1) Polyglycerol-modified silicone: KF-6105, manufactured by Shin-Etsu Chemical Co., Ltd.

(Production Method)
A: Components 1 to 6 were mixed uniformly.
B: Components 7 to 11 were mixed together, and the mixture obtained in A was then added and emulsified.

The W/O cream obtained in this manner suffered no greasiness, was readily spread, exhibited a superior feeling of adhesion to the skin, and had good stability.

Example 71

W/O Makeup Foundation

| (Components) | (%) |
|---|---|
| 1. Cross-linked polyether-modified silicone composition (note 1) | |
| 2. Cross-linked dimethylpolysiloxane composition (note 2) | 1.0 4.0 |
| 3. The organopolysiloxane of example 60 | 1.0 |
| 4. Polyether-modified silicone (note 3) | 0.5 |
| 5. Octyl methoxycinnamate | 6.0 |
| 6. Dimethylpolysiloxane (20 mm²/s (25° C.)) | 2.0 |
| 7. Glyceryl trioctanoate | 3.0 |
| 8. Titanium oxide/cyclopentasiloxane dispersion (note 4) | 10.0 |
| 9. Dipropylene glycol | 5.0 |
| 10. Sodium citrate | 0.2 |
| 11. Methyl cellulose (2% aqueous solution) (note 5) | 2.5 |
| 12. Ethanol | 3.0 |
| 13. Preservative | appropriate amount |
| 14. Fragrance | appropriate amount |
| 15. Pure water | 61.8 |

(note 1) Cross-linked polyether-modified silicone composition: KSG-210 (product name), manufactured by Shin-Etsu Chemical Co., Ltd.
(note 2) Cross-linked dimethylpolysiloxane composition: KSG-16 (product name), manufactured by Shin-Etsu Chemical Co., Ltd.
(note 3) The polyether-modified silicone represented by the formula below.

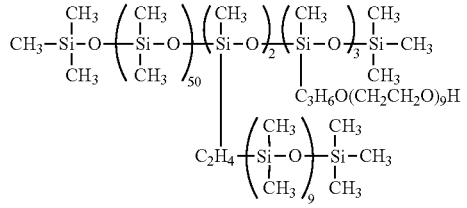

(note 4) Titanium oxide/cyclopentasiloxane dispersion: SPD-T5 (product name), manufactured by Shin-Etsu Chemical Co., Ltd.
(note 5) Methyl cellulose: Metolose 65-SH4000 (product name), manufactured by Shin-Etsu Chemical Co., Ltd.

(Production Method)
A: Components 1 to 8 were mixed together uniformly.
B: Components 9 to 15 were mixed, and then the mixture obtained in A was added and emulsified.

The makeup foundation obtained in this manner suffered no greasiness, was readily spread, and exhibited excellent stability. Moreover, the cosmetic film formed on the skin displayed a matte finish and exhibited excellent adhesion and cosmetic retention.

Example 72

O/W Cream

| (Components) | (%) |
|---|---|
| 1. The organopolysiloxane of example 61 | 5.0 |
| 2. Octyl para-methoxycinnamate | 10.0 |
| 3. Macadamia nut oil | 10.0 |
| 4. Dimethylpolysiloxane (viscosity: 6 mm²/s at 25° C.) | 10.0 |
| 5. Polyglycerol-modified silicone (note 1) | 1.0 |
| 6. Propylene glycol | 3.0 |
| 7. Polyacrylamide-based mixture (note 2) | 0.8 |

-continued

| (Components) | (%) |
|---|---|
| 8. Xanthan gum (2% aqueous solution) | 8.0 |
| 9. Preservative | appropriate amount |
| 10. Fragrance | appropriate amount |
| 11. Pure water | 52.2 |

(note 1) Polyglycerol-modified silicone: KF-6105, manufactured by Shin-Etsu Chemical Co., Ltd.
(note 2) Polyacrylamide-based mixture: Sepigel 305 (product name), manufactured by Seppic Corporation (Production Method)
A: Components 1 to 4 were mixed uniformly.
B: Components 5 to 11 were mixed together.
C: The mixture obtained in A was added to the mixture obtained in B and emulsified.

The O/W cream obtained in this manner exhibited good spreadability and no greasiness, produced a fresh feeling, and exhibited excellent stability.

Example 73

Lipstick

| (Components) | (%) |
|---|---|
| 1. Candelilla wax | 4.0 |
| 2. Polyethylene | 2.0 |
| 3. Microcrystalline wax | 3.0 |
| 4. Ceresin | 7.0 |
| 5. Acrylate/dimethylsilicone copolymer (note 1) | 15.0 |
| 6. The polysiloxane of example 58 | 8.0 |
| 7. Tris(trimethylsiloxy)methylsilane | 8.0 |
| 8. Diisostearyl malate | 30.0 |
| 9. Hydrogenated polyisobutene | 15.0 |
| 10. Octyl para-methoxycinnamate | 4.0 |
| 11. Colorant | appropriate amount |
| 12. Mica | appropriate amount |
| 13. Polyglycerol-modified silicone (note 2) | 4.0 |

(note 1) Acrylate/dimethylsilicone copolymer: KP-561P (manufactured by Shin-Etsu Chemical Co., Ltd.)
(note 2) Polyglycerol-modified silicone: KF-6105, manufactured by Shin-Etsu Chemical Co., Ltd.

(Production Method)
A: Components 6 to 10 were mixed uniformly.
B: Components 1 to 5 were melted under heat at 90° C., and the mixture obtained in A was then added and dispersed uniformly.
C: At 80° C., components 11 to 13 were added to the mixture obtained in B and dispersed uniformly.

The lipstick obtained in this manner exhibited ready spreadability, suffered no greasiness or powderiness, exhibited favorable water resistance and water repellency, offered good cosmetic retention, and also exhibited excellent stability.

Example 74

Non-Aqueous Emulsion

| (Components) | (%) |
|---|---|
| 1. The organopolysiloxane of example 60 | 10.0 |
| 2. Octyl methoxycinnamate | 10.0 |
| 3. Dimethylpolysiloxane (viscosity: 6 mm²/s at 25° C.) | 10.0 |
| 4. Neopentyl glycol dioctanoate | 10.0 |
| 5. Polyglycerol-modified silicone (note 1) | 3.0 |
| 6. Dimethyldistearylammonium hectorite | 2.0 |
| 7. 1,3-butylene glycol | 55.0 |

(note 1) Polyglycerol-modified silicone: KF-6105, manufactured by Shin-Etsu Chemical Co., Ltd.

(Production Method)
A: Components 1 to 6 were mixed uniformly.
B: Component 7 was added to the mixture obtained in A and dispersed uniformly.

The non-aqueous emulsion obtained in this manner exhibited good spreadability and no greasiness, left the skin feeling moist, and exhibited good stability.

INDUSTRIAL APPLICABILITY

The organopolysiloxane of the present invention is useful as a raw material for producing cosmetic materials.

What is claimed is:

1. An organopolysiloxane represented by formula (1) shown below:

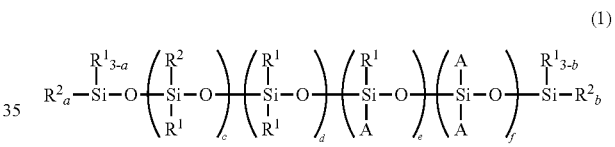

(1)

wherein each $R^1$ independently represents a group selected from the group consisting of $C_1$ to $C_{30}$ alkyl groups, $C_1$ to $C_{30}$ fluorine-substituted alkyl groups, $C_6$ to $C_{30}$ aryl groups, $C_6$ to $C_{30}$ aralkyl groups, and groups represented by formula (i) shown below:

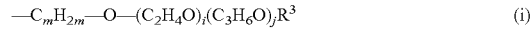

(i)

wherein $R^3$ represents a hydrogen atom, $C_1$ to $C_{30}$ aliphatic hydrocarbon group, or organic group represented by $R^7$—(CO)—, $R^7$ represents a hydrogen atom or $C_1$ to $C_{30}$ aliphatic hydrocarbon group, m represents an integer of 0 to 15, i represents an integer of 0 to 50, and j represents an integer of 0 to 50, each $R^2$ independently represents a group selected from the group consisting of groups represented by formula (3) shown below:

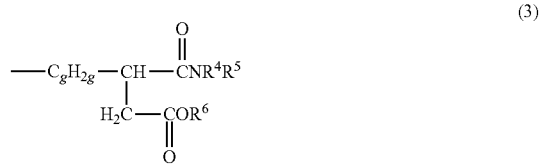

(3)

and groups represented by formula (4) shown below:

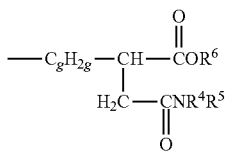
(4)

wherein within formulas (3) and (4), either
$R^4$ represents a $C_8$ to $C_{40}$ aliphatic hydrocarbon group, $C_8$ to $C_{40}$ aryl group, $C_8$ to $C_{40}$ aralkyl group, or group represented by formula (6) shown below:

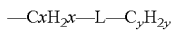
(6)

wherein each of x and y independently represents an integer of 1 to 30, provided that x+y is an integer within a range from 8 to 40, and L represents —NH—, —O—, —COO— or —NHCO—, and $R^5$ represents a hydrogen atom, $C_8$ to $C_{40}$ aliphatic hydrocarbon group, $C_8$ to $C_{40}$ aryl group, $C_8$ to $C_{40}$ aralkyl group, or group represented by formula (6) above, or alternatively $R^4$ and $R^5$ both represent $C_1$ to $C_{12}$ monohydroxyalkyl groups, or $R^4$ represents a $C_1$ to $C_{12}$ dihydroxyalkyl group and $R^5$ represents a hydrogen atom or $C_1$ to $C_{12}$ alkyl group, $R^6$ represents a hydrogen atom, alkali metal atom, ammonium ion or alkylammonium ion, and g represents an integer of 2 to 20, A is a group represented by formula (5) shown below:

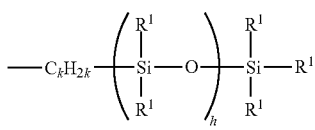
(5)

wherein $R^1$ is as defined above, k represents an integer of 1 to 5, and h represents an integer of 0 to 500,
a and b each represents an integer of 0 to 3,
c represents an integer of 0 to 100, provided that 1 ≤a+b+c,
d represents an integer of 0 to 2,000,
e represents an integer of 0 to 500, and
f represents an integer of 0 to 500.

2. The organopolysiloxane according to claim 1, having a polystyrene-equivalent number average molecular weight determined by GPC within a range from 300 to 300,000.

3. The organopolysiloxane according to claim 1, wherein the organopolysiloxane is represented by formula (2) shown below:

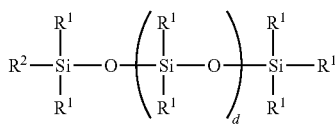
(2)

wherein $R^1$ and $R^2$ are as defined above, and d represents an integer of 0 to 200.

4. The organopolysiloxane according to claim 1, wherein $R^4$ represents a $C_8$ to $C_{40}$ aliphatic hydrocarbon group, $C_8$ to $C_{40}$ aryl group or $C_8$ to $C_{40}$ aralkyl group, and $R^5$ represents a hydrogen atom, $C_8$ to $C_{40}$ aliphatic hydrocarbon group, $C_8$ to $C_{40}$ aryl group or $C_8$ to $C_o$ aralkyl group.

5. The organopolysiloxane according to claim 1, wherein $R^1$ represents a methyl group or a butyl group, $R^4$ represents a $C_8$ to $C_{20}$ alkyl group, and $R^5$ and $R^6$ are both hydrogen atoms.

6. The organopolysiloxane according to claim 1, wherein $R^4$ and $R^5$ both represent $C_1$ to $C_{12}$ monohydroxyalkyl groups, or $R^4$ represents a $C_1$ to $C_{12}$ dihydroxyalkyl group and $R^5$ represents a hydrogen atom or $C_1$ to $C_{12}$ alkyl group.

7. The organopolysiloxane according to claim 1, wherein $R^1$ represents a methyl group or a butyl group, $R^4$ represents a 1,3-propanediol-2-yl group or 1,2-propanediol-3-yl group, and $R^5$ and $R^6$ are both hydrogen atoms.

8. The organopolysiloxane according to claim 1, wherein $R^1$ represents a methyl group, $R^4$ and $R^5$ are both methylol groups, and $R^6$ is a hydrogen atom.

9. A cosmetic material, comprising the organopolysiloxane defined in claim 1 in an amount equivalent to 0.1 to 40% by mass of a total mass of the cosmetic material.

10. The cosmetic material according to claim 9, further comprising water and existing as an emulsion.

11. The cosmetic material according to claim 9, further comprising an ester oil, glyceride oil or mixture thereof, and existing as a non-aqueous emulsion.

12. The cosmetic material according to claim 9, further comprising a powder, and existing as a liquid, a paste or a solid.

13. The cosmetic material according to claim 11, further comprising a powder, and existing as a liquid, a paste or a solid.

14. The cosmetic material according to claim 9, wherein the cosmetic material is used for skin care.

15. The organopolysiloxane according to claim 1, having the formula

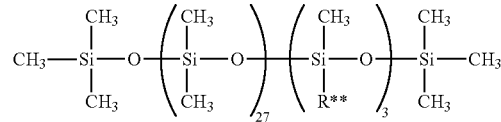

wherein

R**: 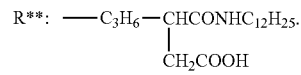

* * * * *